US009216211B2

(12) United States Patent
Hause

(10) Patent No.: US 9,216,211 B2
(45) Date of Patent: Dec. 22, 2015

(54) ATTENUATED SWINE INFLUENZA VACCINES AND METHODS OF MAKING AND USE THEREOF

(71) Applicant: Benjamin M Hause, Currie (MN)

(72) Inventor: Benjamin M Hause, Currie (MN)

(73) Assignee: MERIAL, INC., Duluth, GA (US)

( * ) Notice: Subject to any disclaimer, the term of this patent is extended or adjusted under 35 U.S.C. 154(b) by 87 days.

(21) Appl. No.: 13/939,321

(22) Filed: Jul. 11, 2013

(65) Prior Publication Data

US 2014/0023681 A1    Jan. 23, 2014

Related U.S. Application Data

(60) Provisional application No. 61/672,398, filed on Jul. 17, 2012.

(51) Int. Cl.
| | |
|---|---|
| *A61K 39/145* | (2006.01) |
| *A61K 39/02* | (2006.01) |
| *A61K 39/21* | (2006.01) |
| *A61K 39/12* | (2006.01) |
| *C12N 7/04* | (2006.01) |
| *A61K 39/00* | (2006.01) |

(52) U.S. Cl.
CPC ........... *A61K 39/145* (2013.01); *A61K 39/0241* (2013.01); *A61K 39/12* (2013.01); *A61K 39/21* (2013.01); *C12N 7/04* (2013.01); *A61K 2039/5254* (2013.01); *A61K 2039/552* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 5,585,250 | A | 12/1996 | Garrity et al. |
| 5,853,724 | A | 12/1998 | Garrity et al. |
| 7,723,094 | B2 | 5/2010 | Kawaoka et al. |
| 2011/0177121 | A1 | 7/2011 | Nara et al. |
| 2014/0023681 | A1* | 1/2014 | Hause ................. 424/209.1 |

FOREIGN PATENT DOCUMENTS

WO    WO 2011/091376 A2    7/2011

OTHER PUBLICATIONS

De Vleeschauwer et al. (Influenza and Other Respiratory Viruses. 2011; 5 (2): 115-122).*
Yu et al. (Journal of Clinical Microbiology. 2008; 46 (3): 1067-1075).*
Schultze (Journal of Infectious Diseases. 1997; 176 (Supple. 1): S24-28).*
Inkster et al. (Journal of Virology. 1993; 67 (12): 7436-7443).*
Sequence alignment of instant Seq Id No: 22 with Geneseq database acc. No. AWW92142, Jun. 2009.*
Sequence alignment of Seq Id No: 24 with Geneseq database access No. AYN41072, Feb. 2011.*
Das SR et al. Glycosylation Focuses Sequence Variation in the Influenza A Virus H1 Hemagglutinin Globular Domain. PLOS Pathogens. Nov. 2010 | vol. 6 | Issue 11 | e1001211.
Das SR et al. Fitness costs limit influenza A virus hemagglutinin glycosylation as an immune evasion strategy. PNAS | Dec. 20, 2011 | vol. 108 | No. 51 | E1417-E1422.
Lin S-C et al. Broader Neutralizing Antibodies against H5N1 Viruses Using Prime-Boost Immunization of Hyperglycosylated Hemagglutinin DNA and Virus-Like Particles. Jun. 2012 | vol. 7 | Issue 6.
Garrity et al. Refocusing Neutralizing Antibody Response by Targeted Dampening of an Immunodominant Epitope. J. Immunology. pp. 279-289. 1997.
Samji T. Influenza A: Understanding the Viral Life Cycle. Yale Journal of Biology and Medicine 82 (2009), pp. 153-159.
Vigerust et al. N-Linked Glycosylation Attenuated H3N2 Influenza Viruses. Journal of Virology, Aug. 2007, p. 8593-8600.
Zhou B et al. Reverse genetics plasmid for cloning unstable Influenza A virus gene segments. Journal of Virological Methods 173 (2011) 378-383.
Selvarajah S et al. Focused dampening of antibody response to the immunodominant variable loops by engineered soluble gp140. AIDS Res Hum Retroviruses. Feb. 2008;24(2):301-14.
Lin G et al. Designing immunogens to elicit broadly neutralizing antibodies to the HIV-1 envelope glycoprotein. Only abstract provided. Curr HIV Res. Nov. 2007;5(6):514-41.
Trujillo JD et al. Glycosylation of immunodominant linear epitopes in the carboxy-terminal region of the caprine arthritis-encephalitis virus surface envelope enhances vaccine-induced type-specific and cross-reactive neutralizing antibody responses. J Virol. Sep. 2004;78(17):9190-202.
Abe Y et al. 2004. Effect of the addition of oligosaccharides on the biological activities and antigenicity of influenza A/H3N2 virus hemagglutinin. J. Virology 78:9605-9611.
Bohne-Lang A, von der Lieth CW. 2005. GlyProt: in silico glycosylation of proteins. Nucleic Acids Res. 33:W214-219.
Bragstad K et al. 2008. The evolution of human influenza A viruses from 1999 to 2006: A complete genome study. Virology J. 5:40.
Cai Z et al. 2010. A computational framework for influenza antigenic cartography. PLoS Computational Biology, 6(10):e1000949.
Caton AJ et al. 1982. The antigenic structure of the influenza virus A/PR/8/34 hemagglutinin (H1 subtype). Cell 31:417-427.
Desselberger U et al. 1978. Biochemical evidence that "new" influenza virus strains in nature may arise by recombination (reassortment). Proc. Natl. Acad. Sci. 75:3341-3345.
Hause BM et al. 2011. Genetic and antigenic characterization of recent human-like H1 (δ-cluster) swine influenza virus isolates. J. Swine Health Prod. 19:268-276.

(Continued)

*Primary Examiner* — Shanon A Foley
(74) *Attorney, Agent, or Firm* — Judy Jarecki-Black; Chad Kitchen; Merial, Inc.

(57) ABSTRACT

This disclosure provides attenuated swine influenza strains, particularly those produced via a reverse genetics approach, compositions comprising same, and methods of production and use thereof. The attenuated strains are engineered to encode HA proteins having additional glycosylation sites, relative to the HA proteins encoded by the corresponding virulent parental viruses. Advantageously, the attenuated influenza strains may be administered.

12 Claims, 3 Drawing Sheets

(56) References Cited

OTHER PUBLICATIONS

Hause BM et al. 2010. Antigenic categorization of contemporary H3N2 swine influenza virus isolates using a high-throughput serum neutralization assay. J. Vet. Diagn. Invest. 22:352-359.
Hay AJ et al. 2001. The evolution of human influenza viruses. Philos. T. R. Soc. B. 356:1861-1870.
Hensley SE et al. 2011. Influenza A virus hemagglutinin antibody escape promotes neuraminidase antigenic variation and drug resistance. PLoS ONE 6:e15190.
Hoffmann E et al. 2001. Universal primer set for the full length amplification of al influenza viruses. Arch. Virol. 146:2275-2289.
Hoffmann E et al. 2000. A DNA transfection system for generation of influenza A virus from eight plasmids. Proc. Natl. Acad. Sci. 97:6108-6113.
Karasin AI et al. 2006. Identification of human H1N2 and human-swine reassortant H1N2 and H1N1 influenza A viruses among pigs in Ontario, Canada (2003-2005). J. Clin. Microbiol. 44:1123-1126.
Long J et al. 2011. Evolution of H3N2 influenza virus in a guinea pig model. PLoS ONE 6:e20130.
Schulze IT. 1997. Effects of glycosylation on the properties and functions of influenza virus hemagglutinin J. Infect. Dis. 176:S24-S28.
Strengell M et al. 2011. Minor changes in the hemagglutinin of influenza A(H1N1)2009 virus alter its antigenic properties. PLoS ONE 6:e25848.
Sun S et al. 2011. Glycosylation site alteration in the evolution of influenza A (H1N1) viruses. PLoS ONE 6:e22844.
Sun S et al. 2012. Prediction of biological functions on glycosylation site migrations in human influenza H1N1 viruses. PLoS ONE 7:e32119.
Who Manual on Animal Influenza Diagnosis and Surveillance, 2002 (http://whqlibdoc.who.int/hq/2002/WHO_CDS_CSR_NCS_2002.5.pdf).
Tamura K et al. 2011. MEGA5: Molecular evolutionary genetics analysis using maximum likelihood, evolutionary distance, and maximum parsimony methods. Mol. Biol. Evol. 28: 2731-2739.
Vincent AL et al. 2009. Characterization of a newly emerged genetic cluster of H1N1 and H1N2 swine influenza virus in the United States. Virus Genes 39:176-185.
Wagner R et al. 2000. Interdependence of hemagglutinin glycosylation and neuraminidase as regulators of influenza virus growth: a study by reverse genetics. J. Virology 74:6316-6323.
Wanzeck K et al. 2011. Glycan shielding of the influenza virus hemagglutinin contributes to immunopathology in mice. Am. J. Respir. Crit. Care Med. 183:767-773.
Wei C-J et al. 2010. Cross-neutralization of 1918 and 2009 influenza viruses: role of glycans in viral evolution and vaccine design. Sci. Trans. Med. 2:24fa21. doi:10.1126/scitranslmed.3000799.
Zhou B et al. 2009. Single-reaction genomic amplification accelerates sequencing and vaccine production for classical and swine origin human influenza A viruses. J. Virology 83:10309-10313.
Vincent et al. "Efficacy of intranasal administration of a truncated NS1 modified live influenza virus vaccine in swine", Vaccine, Elsevier Ltd, GB, vol. 25, No. 47, Oct. 26, 2007, pp. 7999-8009.
Sun Xiangjie et al. "N-Linked Glycosylation of the Hemagglutinin Protein Influences Virulence and Antigenicity of the 1918 Pandemic and Seasonal H1 N1 Influenza A Viruses", Journal of Virology, The American Society for Microbiology, US, vol. 87, No. 15, Aug. 1, 2013, pp. 8756-8766.
Long J et al. "Evolution of H3N2 Influenza Virus in a Guinea Pig Model." PLOS One. Jul. 2011 | vol. 6 | Issue 7 | e20130.
Nara PL et al. "How Can Vaccines Against Influenza and Other Viral Diseases Be Made More Effective?" PLOS One. Dec. 2010 | vol. 8 | Issue 12 | e1000571.
Pan K et al. "Selective Pressure to Increase Charge in Immunodominant Epitopes of the H3 Hemagglutinin Influenza Protein." J Mol Evol (2011) 72:90-103.
Bushnell RV et al. "Serological characterization of guinea pigs infected with H3N2 human influenza or immunized with hemagglutinin protein." Virology Journal 2010, 7:200.
Tobin GJ et al. "Deceptive imprinting and immune refocusing in vaccine design." Vaccine 26 (2008) 6189-6199.

\* cited by examiner

```
PB2
PB1
PA
HA
NP
NA
M
NS
```

▓▓▓ A/swine/North Carolina/3793/08
░░░ 10-0036-2

*FIG. 1*

Seq 18 = HA (parent); Seq 22 = HA (n+5 mutant)

```
SEQ 18   MKVKLMVLLCTFTATYADTICVGYHANNSTDTVDTVLEKNVTVTHSVNLLEDSHNGKLCL   60
SEQ 22   MKVKLMVLLCTFTATYADTICVGYHANNSTDTVDTVLEKNVTVTHSVNLLEDSHNGKLCL   60

SEQ 18   LKGIAPLQLGSCSVAGWILGNPECELLISKESWSYIVETPNPENGTCYPGYFTDYEELRE   120
SEQ 22   LKGIAPLQLGNCSVAGWILGNPECELLISNESWSYIVETPNPENGTCYPGYFTDYEELRE   120

SEQ 18   QLSSVSSFKRFEIFPKESSWPNHTVTGVSSSCSHNGKSSFYRNLLWLTVKNGLYPNLSKS   180
SEQ 22   QLSSVSSFKRFEIFPKESSWPNHTVTGVSSSCSHNGKSSFYRNLLWLTVKNGTYPNLSKS   180

SEQ 18   YTNKKEKEVLVLWGVHHPSNIGDQRALYHTENAYVSVVSSHYSRRFTPEIAKRPKVRNQE   240
SEQ 22   YTNKKEKEVLVLWGVHHPSNIGDQRALYHTENAYVSVVSSHYSRRFTPEIAKRPKVRNQE   240

SEQ 18   GRINYYWTLLEPGDTIIFEANGNLIAPRYAFELSKGFGSGIITSNAPMGECNAKCQTPQG   300
SEQ 22   GRINYYWTLLEPGDTIIFEANGNLIAPRYAFELSKGFGSGIITSNATMGECNATCQTPQG   300

SEQ 18   AINSSLPFQNVHPVTIGECPKYVKSAKLRMVTGLRNTPSIQSRGLFGAIAGFIEGGWTGM   360
SEQ 22   AINSSLPFQNVHPVTIGECPKYVKSAKLRMVTGLRNTPSIQSRGLFGAIAGFIEGGWTGM   360

SEQ 18   VDGWYGYHHQNEQGSGYAADQQSTQNAINGITNKVNSVIEKMNTQFTAVGKEFNKLERRM   420
SEQ 22   VDGWYGYHHQNEQGSGYAADQQSTQNAINGITNKVNSVIEKMNTQFTAVGKEFNKLERRM   420

SEQ 18   ENLNKKVDDGFLDIWTYNAELLVLLENERTLDFHDSNVKNLYEKVKSQLKNNAKEIGNGC   480
SEQ 22   ENLNKKVDDGFLDIWTYNAELLVLLENERTLDFHDSNVKNLYEKVKSQLKNNAKEIGNGC   480

SEQ 18   FEFYHKCNDECMESVKNGTYDYPKYSEESKLNREKIDGVKLESMGVYNILAIYSTVASSL   540
SEQ 22   FEFYHKCNDECMESVKNGTYDYPKYSEESKLNREKIDGVKLESMGVYNILAIYSTVASSL   540

SEQ 18   VLLVSLGAISFWMCSNGSLQCRICI   565
SEQ 22   VLLVSLGAISFWMCSNGSLQCRICI   565
```

*FIG. 2*

Hyperglycosylation Growth Study. Lines represent mutants with additional engineered N-linked glycosylation sites

|   | Rescued virus | additional glycosylation sites (n) |
|---|---|---|
| 0 | RG parent (10-0036-2) | 0 |
| 1 | S71N | 1 |
| 2 | S71N, K90N | 2 |
| 3 | S71N, K90N, L173T | 3 |
| 4 | S71N, K90N, L173T, P287T | 4 |
| 5 | S71N, K90N, L173T, P287T, K294T | 5 |

*FIG. 3*

| SEQ ID NO | TYPE | DESCRIPTION |
|---|---|---|
| 1 | DNA | PB2 gene of Influenza A/swine/NorthCarolina/3793/08(H1N1) - 10-0036-2 |
| 2 | PRT | PB2 predicted AA of Influenza A/swine/NorthCarolina/3793/08(H1N1) - 10-0036-2 |
| 3 | DNA | PB1 gene of Influenza A/swine/NorthCarolina/3793/08(H1N1) - 10-0036-2 |
| 4 | PRT | PB1 predicted AA of Influenza A/swine/NorthCarolina/3793/08(H1N1) - 10-0036-2 |
| 5 | DNA | PA gene of Influenza A/swine/NorthCarolina/3793/08(H1N1) - 10-0036-2 |
| 6 | PRT | PA predicted AA of Influenza A/swine/NorthCarolina/3793/08(H1N1) - 10-0036-2 |
| 7 | DNA | HA gene of Influenza A/swine/NorthCarolina/3793/08(H1N1) - 10-0036-2 |
| 8 | PRT | HA predicted AA of Influenza A/swine/NorthCarolina/3793/08(H1N1) - 10-0036-2 |
| 9 | DNA | NP gene of Influenza A/swine/NorthCarolina/3793/08(H1N1) - 10-0036-2 |
| 10 | PRT | NP predicted AA of Influenza A/swine/NorthCarolina/3793/08(H1N1) - 10-0036-2 |
| 11 | DNA | NA gene of Influenza A/swine/NorthCarolina/3793/08(H1N1) - 10-0036-2 |
| 12 | PRT | NA predicted AA of Influenza A/swine/NorthCarolina/3793/08(H1N1) - 10-0036-2 |
| 13 | DNA | M gene of Influenza A/swine/NorthCarolina/3793/08(H1N1) - 10-0036-2 |
| 14 | PRT | M predicted AA of Influenza A/swine/NorthCarolina/3793/08(H1N1) - 10-0036-2 |
| 15 | DNA | NS gene of Influenza A/swine/NorthCarolina/3793/08(H1N1) - 10-0036-2 |
| 16 | PRT | NS predicted AA of Influenza A/swine/NorthCarolina/3793/08(H1N1) - 10-0036-2 |
| 17 | DNA | HA gene of Influenza 10-0036-2 (n+0, parent) - RG 10-0036-2 |
| 18 | PRT | HA predicted AA of Influenza 10-0036-2 (n+0, = parent) - RG 10-0036-2 |
| 19 | DNA | NA gene of Influenza 10-0036-2 (n+0, parent) - RG 10-0036-2 |
| 20 | PRT | NA predicted AA of Influenza 10-0036-2 (n+0, = parent) - RG 10-0036-2 |
| 21 | DNA | HA gene of Influenza 10-0036-2 (n+5, relative to RG 10-0036-2) |
| 22 | PRT | HA predicted AA of Influenza 10-0036-2 (n+5, relative to RG 10-0036-2) |
| 23 | DNA | HA gene of Influenza 10-0036-2 (n+4, relative to RG 10-0036-2) |
| 24 | PRT | HA predicted AA of Influenza 10-0036-2 (n+4, relative to RG 10-0036-2) |
| 25 | DNA | HA gene of Influenza 10-0036-2 (n+3, relative to RG 10-0036-2) |
| 26 | PRT | HA predicted AA of Influenza 10-0036-2 (n+3, relative to RG 10-0036-2) |
| 27 | DNA | HA gene of Influenza 10-0036-2 (n+2, relative to RG 10-0036-2) |
| 28 | PRT | HA predicted AA of Influenza 10-0036-2 (n+2, relative to RG 10-0036-2) |
| 29 | DNA | HA gene of Influenza 10-0036-2 (n+1, relative to RG 10-0036-2) |
| 30 | PRT | HA predicted AA of Influenza 10-0036-2 (n+1, relative to RG 10-0036-2) |

*FIG. 4*

ATTENUATED SWINE INFLUENZA VACCINES AND METHODS OF MAKING AND USE THEREOF

INCORPORATION BY REFERENCE

This application claims priority to provisional application U.S. Ser. No. 61/672,398, filed on Jul. 17, 2012, and incorporated by reference herein in its entirety.

FIELD OF THE INVENTION

The present invention relates generally to attenuated viral vaccines, particularly those providing broad, safe, and effective protection to porcines against infections/disease caused by swine influenza. The invention further relates to methods of producing the attenuated viruses, and to the identification of nucleic acid variations that are associated with decreased virulence of the attenuated virus.

The invention accordingly relates to immunogenic or vaccine compositions comprising the viruses of the invention; e.g., live attenuated virus. The viruses also could be inactivated in the compositions; but it may be advantageous that the viruses are live attenuated swine influenza. The invention therefore further relates to methods for preparing and/or formulating such compositions; e.g., culturing or growing or propagating the viruses on or in suitable medium, harvesting the viruses, optionally inactivating the viruses, and optionally admixing with a suitable veterinarily or pharmaceutically acceptable carrier, excipient, diluent or vehicle and/or an adjuvant and/or stabilizer. Thus, the invention also relates to the use of the viruses in formulating such compositions.

BACKGROUND OF THE INVENTION

Influenza viruses possess a number of mechanisms to elude host humoral immunity against hemagglutinin (HA) that mediates viral entry. Reassortment of genome segments can lead to antigenic shift while gradual accumulation of mutations leads to genetic drift (Desselberger U, et al. 1978, Schild G, et al. 1974). In addition to mutations in the antigenic epitopes of the HA that can impact the ability of pre-existing antibodies to recognize mutant HA, mutations in N-linked glycosylation of HA can promote viral evasion of antibody recognition by altering the oligosaccharide layer surrounding the HA (Schulze I T, 1997). Glycan residues can restrict the binding of some antibodies to their epitopes, leading to loss of antibody recognition and immunogenicity in a phenomenon known as glycan shielding (Wanzeck K, et al. 2011, Wei C-J, et al. 2010). Additionally, mutation and genetic drift preferentially occur at positions in the HA globular head that are not protected by glycans (Das S R, et al. 2010). Glycan residues also influence receptor binding and consequently can affect viral replication kinetics.

The evolution of influenza viruses frequently includes modification of the number and position of glycosylation sites (Long J, et al. 2011). For H3N2 viruses, the number of glycosylation sites has increased from two to ten over the last 40 years (4). However, increasingly glycosylated HA has been correlated with decreased virulence in mice and reduced viral fitness (Das S R, et al. 2011, Vigerust D J, et al. 2007). While increasing glycosylation can shield HA from neutralizing antibodies, the viral affinity for cellular receptors is obligatorily decreased (Abe Y, et al. 2004, Das S R, et al. 2011). Also, compensatory mutations in either the HA or neuraminidase (NA) are required to balance receptor binding and release activities (Wagner R, et al. 2000). These compensatory mutations in NA have been associated with the acquisition of natural resistance to NA inhibitors (Hensley S E, et al. 2011).

Numerous genetic and antigenically distinct lineages of swine influenza virus circulate concurrently in pigs, including β, γ and δ-cluster H1N1 and H1N2 viruses, as well as the H3N2 subtype (Lorusso A, et al. 2012). The δ-cluster was originally subdivided into two subclusters (δ-I and δ-II), however, more recent work demonstrated five distinct genetic subclusters (δ-A, δ-B, δ-C, δ-D, δ-E) representing at least three antigenically distinct groups (Hause B M, et al. 2011, Vincent A L, et al. 2009).

While killed viral vaccines are efficacious when the vaccine strains match the field challenge virus, the rapid mutation rate of influenza requires frequent strain changes to ensure genetic and antigenic match between the vaccine strains and circulating viruses. Additionally, the multiple subtypes and lineages co-circulating in swine frequently require five or more vaccine strains in order to include representatives of each type. A single live vaccine that elicits broad spectrum immunity offer a significant advance in swine health programs.

SUMMARY OF THE INVENTION

An object of this invention is to provide attenuated vaccines as well as methods for treatment and prophylaxis of infection by swine influenza.

In an embodiment, the vaccines comprise attenuated influenza viruses, which have been modified to express HA genes having additional glycosylation sites relative to their parental strain.

In a particular embodiment, the HA genes and/or gene products have the same modifications as are present between SEQ ID NOs:17 and 21; SEQ ID NOs:17 and 23; SEQ ID NOs:18 and 22; or SEQ ID NOs:18 and 24. In yet another embodiment, the HA genes and/or gene products have at least 1 out of the 5 modifications. In a more particular embodiment, the HA genes and/or gene products have 4 or 5 of the modifications, results in +4 and +5 glycosylation sites, relative to the parent HA gene products.

Another object of this invention is to provide cDNA and/or plasmids for use in a reverse genetics system for producing attenuated influenza according to the instant disclosure. In an embodiment, at least one of the cDNA and/or plasmids comprises a HA sequence having increased number of glycosylation sites relative to the sequence as set forth in SEQ ID NO:18.

In a particular embodiment, the HA sequence is as set forth in SEQ ID NOs:21 or 23.

The present invention further relates to new attenuated strains of Influenza, which provide safe, effective, and broad protective immunity. Relative to a parent Influenza strain, the attenuated strains may have additional glycosylation sites and/or putative glycosylation sites encoded by their HA genes, whose presence is associated with reduced virulence.

Thus, the invention provides a mutant virus comprising a mutation(s) in one or more nucleic acids sequences, relative to the wild type/parental virus, which renders the mutant virus attenuated, relative to the parent virus, which parent virus comprises nucleic acids encoding a wild type HA protein. As defined herein, the "wild type" HA protein is one having the same number of glycosylation sites and/or putative glycosylation sites relative to the sequences as set forth in SEQ ID NO:18.

In a particular embodiment, the mutant virus comprises vRNA nucleic acid sequences which correspond to (i.e. are reverse complementary and have uracils in place of thymidines) the DNA sequences set forth in SEQ ID NOs:21 or 23, which encode for peptides as set forth in SEQ ID NOs:22 or 24, respectively, and which cause the mutant virus to be attenuated/non-virulent, relative to the virulent wild type/parental virus.

As defined herein, the term "gene" will be used in a broad sense, and shall encompass both coding and non-coding sequences (i.e. upstream and downstream regulatory sequences, promoters, 5'/3' UTR, introns, and exons). Where reference to only a gene's coding sequence is intended, the term "gene's coding sequence" or "CDS" will be used interchangeably throughout this disclosure. When a specific nucleic acid is discussed, for example, the sequence as set forth in SEQ ID NO:17 (the DNA sequence equivalent of parental virus cRNA "sense" strand), the skilled person will instantly be in possession of all derivable forms of that sequence (mRNA, vRNA, cRNA, DNA, protein, etc.). For example, the influenza virus is a negative single strand RNA virus (ssRNA). To replicate, its negative ssRNA (defined herein as "vRNA") must be transcribed to positive or sense RNA (defined herein as "cRNA"). Host cell machinery is co-opted to use the cRNA to produce the viral proteins and vRNA. A skilled person using the well-known genetic code can routinely derive from a DNA sequence the vRNA, cRNA, and peptide sequences.

In a particular embodiment, the attenuated vaccines comprise an adjuvant. The adjuvant may be any substance which increases and/or augments the elicited immune response, as compared to attenuated vaccine alone. Mucosal adjuvants, including chitosans and derivatives thereof, are particularly useful for the disclosed oral attenuated vaccines.

The invention further provides methods for inducing an immunological (or immunogenic) or protective response against Influenza, as well as methods for preventing or treating Influenza, or disease state(s) caused by Influenza, comprising administering the attenuated virus, or a composition comprising the attenuated virus to animals in need thereof.

Kits comprising at least the attenuated Influenza strain and instructions for use are also provided.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 1 presents the genotype of viruses created using reverse genetics;

FIG. 2 is an amino acid alignment between SEQ ID NO:18 (HA protein of parent influenza virus) and SEQ ID NO:22 (HA protein of n+5 glycosylation mutant);

FIG. 3 is a graph of the growth in cultured cells of parent and glycosylation mutant influenza viruses harboring between 1 and 5 additional glycosylation sites in their HA gene, relative to parent;

FIG. 4 is a table listing the SEQ ID of this disclosure.

DETAILED DESCRIPTION OF THE INVENTION

The present invention provides nucleotide sequences and genes involved in the attenuation of a microorganism, such as virus, for instance, Influenza, products (e.g., proteins, antigens, immunogens, epitopes) encoded by the nucleotide sequences, methods for producing such nucleotide sequences, products, micro-organisms, and uses therefore, such as for preparing vaccine or immunogenic compositions or for eliciting an immunological or immune response or as a vector, e.g., as an expression vector (for instance, an in vitro or in vivo expression vector).

Mutations introduced into nucleotide sequences and genes of micro-organisms produce novel and nonobvious attenuated mutants. These mutants are useful for the production of live attenuated immunogenic compositions or live attenuated vaccines having a high degree of immunogenicity.

Identification of the mutations provides novel and nonobvious nucleotide sequences and genes, as well as novel and nonobvious gene products encoded by the nucleotide sequences and genes.

In an embodiment, the invention provides an attenuated hyperglycosylated swine influenza strain capable of providing a safe and effective immune response in porcine against influenza or diseases caused by influenza. In one embodiment, the strain may encode an HA gene having at least 1 additional glycosylation site relative to virulent parental strain.

In another embodiment, the attenuated strain may encode an HA gene having 4 or 5 additional glycosylation sites relative to virulent parental strain. In a particular embodiment, the strain glycosylation sites are selected from S71N, K90N, L173T, P287T, and K294T, with the locations of the Amino Acid changes being based upon an HA gene having the sequence as set forth in SEQ ID NO:18.

In one embodiment, the HA protein produced by the attenuated influenza strain has the sequence as set forth in SEQ ID NO:22 or a sequence with at least 90% homology to SEQ ID NO:22 provided the following locations have the following amino acids: 71N, 90N, 173T, 287T, and 294T.

In another embodiment, the attenuated influenza produces an HA protein having the sequence as set forth in SEQ ID NO:24 or a sequence with at least 90% homology to SEQ IN NO:24 provided the following locations have the following amino acids: 71N, 90N, 173T, 287T.

In another aspect, the invention provides immunological composition comprising attenuated influenza strains, which encode hyperglycosylated HA proteins. In one embodiment, the compositions may further comprise a pharmaceutically or veterinary acceptable vehicle, diluent or excipient.

In an embodiment, the composition provides a protective immune response in porcine against virulent swine influenza challenge. In some embodiments, the composition further comprises at least one additional antigen associated with a pathogen other than swine influenza.

In another embodiment, the at least one additional antigen is selected from M. hyo, PCV2, PRRSV, SIV or other pathogen capable of infecting and causing illness or susceptibility to illness in a porcine, or combinations thereof.

In an embodiment, the invention provides methods of vaccinating an animal comprising at least one administration of the compositions comprising sequences encoding hyperglycosylated influenza HA proteins. In another embodiment, the porcine is a sow from about 3 weeks to about 6 weeks pre-farrowing. In yet another embodiment, the resulting piglets may have a reduced morbidity and/or mortality as compared to piglets coming from unvaccinated sows.

In another embodiment, the invention provides a composition comprising a plurality of vectors for production of attenuated swine influenza including a vector comprising a promoter operably linked to an influenza virus HA cDNA, wherein the HA cDNA encodes additional glycosylation sites relative to an HA encoded by a virulent parent swine influenza strain. In one particular embodiment, the additional glycosylation sites are selected from S71N, K90N, L173T, P287T, and K294T, and the location of the Amino Acid changes is based upon an HA gene having the sequence as set forth in SEQ ID NO:18.

In an embodiment, the HA cDNA for producing attenuated influenza encodes the protein as set forth in SEQ ID NO:22. In another embodiment, HA cDNA encodes the protein as set forth in SEQ ID NO:24.

In an embodiment, the invention provides a method to prepare influenza virus, comprising: contacting a cell with one of the inventive compositions in an amount effective to yield infectious influenza virus. In one embodiment, the method further comprises isolating the virus.

In another embodiment, the invention provides a method to prepare a gene delivery vehicle, comprising: contacting cells with the inventive composition in an amount effective to yield influenza virus, and isolating the virus. The invention further provides a cell contacted with the inventive composition.

In an embodiment, the invention provides a vertebrate cell comprising a plurality of vectors for production of attenuated swine influenza including a vector comprising a promoter operably linked to an influenza virus HA cDNA, wherein the HA cDNA encodes additional glycosylation sites relative to an HA encoded by a virulent parent swine influenza strain.

The invention further encompasses gene products, which provide antigens, immunogens and epitopes, and are useful as isolated gene products.

Such isolated gene products, as well as epitopes thereof, are also useful for generating antibodies, which are useful in diagnostic applications.

Such gene products, which can provide or generate epitopes, antigens or immunogens, are also useful for immunogenic or immunological compositions, as well as vaccines.

In an aspect, the invention provides viruses containing an attenuating mutation in a nucleotide sequence or a gene wherein the mutation modifies the biological activity of a polypeptide or protein encoded by a gene, resulting in attenuated virulence of the virus.

In particular, the present invention encompasses attenuated swine influenza strains and vaccines comprising the same, which elicit an immunogenic response in an animal, particularly the attenuated swine influenza strains that elicit, induce or stimulate a response in a porcine.

Particular swine influenza attenuated strains of interest have mutations in genes, relative to wild type virulent parent strain, which are associated with virulence. It is recognized that, in addition to strains having the disclosed mutations, attenuated strains having any number of mutations in the disclosed virulence genes can be used in the practice of this invention.

In another aspect, the novel attenuated swine influenza strains are formulated into safe, effective vaccine against swine influenza and infections/diseases cause by swine influenza.

In an embodiment, the swine influenza vaccines further comprise an adjuvant. In a particular embodiment, the adjuvant is a mucosal adjuvant, such as chitosan, methylated chitosan, trimethylated chitosan, or derivatives or combinations thereof.

In an embodiment, the adjuvant comprises whole bacteria and/or viruses, including H. parasuis, clostridium, swine influenza virus (SIV), porcine circovirus (PCV), porcine reproductive and respiratory syndrome virus (PRRSV), *Mannheimia, Pasteurella, Histophious, Salmonella, Escherichia coli*, or combinations and/or variations thereof. In several embodiments, the adjuvant increases the animal's production of IgM, IgG, IgA, and/or combinations thereof.

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a swine influenza vaccine or composition which may comprise an attenuated swine influenza strain and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of use and Article of Manufacture

The present invention includes the following method embodiments. In an embodiment, a method of vaccinating an animal comprising administering a composition comprising an attenuated swine influenza strain and a pharmaceutical or veterinarily acceptable carrier, excipient, or vehicle to an animal is disclosed. In one aspect of this embodiment, the animal is a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of pig or swine compositions, based on viral antigens, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as porcine, with a virulent strain of swine influenza. Both homologous and heterologous strains are used for challenge to test the efficacy of the vaccine. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of swine influenza-specific antibody.

The compositions comprising the attenuated viral strains of the invention used in the prime-boost protocols are contained in a pharmaceutically or veterinary acceptable vehicle, diluent or excipient. The protocols of the invention protect the animal from swine influenza and/or prevent disease progression in an infected animal.

The various administrations are preferably carried out 1 to 6 weeks apart. Preferred time interval is 3 to 5 weeks, and optimally 4 weeks according to one embodiment, an annual booster is also envisioned. The animals, for example pigs, may be at least 3-4 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against swine influenza in an animal comprising an attenuated swine influenza immunological composition or vaccine and instructions for performing the method of delivery in an effective amount for eliciting an immune response in the animal.

Another embodiment of the invention is a kit for performing a method of inducing an immunological or protective response against swine influenza in an animal comprising a composition or vaccine comprising an attenuated swine influenza strain of the invention, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912).

REFERENCES

Abe Y, Takashita E, Sugawara K, Matsuzaki Y, Muraki Y, Hongo S. 2004. Effect of the addition of oligosaccharides on the biological activities and antigenicity of influenza A/H3N2 virus hemagglutinin. J. Virology 78:9605-9611.

Altschul S F, Madden T L. 1997. Gapped BLAST and PSI-BLAST: a new generation of protein database search programs. Nucleic Acids Res. 25:3389-3402.

Bohne-Lang A, von der Lieth C W. 2005. GlyProt: in silico glycosylation of proteins. Nucleic Acids Res. 33:W214-219.

Bragstad K, Nielsen L P, Fomsgaard A. 2008. The evolution of human influenza A viruses from 1999 to 2006: A complete genome study. Virology J. 5:40.

Cai Z, Zhang T, Wan X-F. 2010. A computational framework for influenza antigenic cartography. PLoS Computational Biology, 6(10):e1000949.

Caton A J, Brownlee G G, Yewdell J W, Gerhard W. 1982. The antigenic structure of the influenza virus A/PR/8/34 hemagglutinin (H1 subtype). Cell 31:417-427.

Cottey R, Rowe C A, Bender B S. 2001. Influenza virus. Curr. Protoc. Immunol. 19.11:1-32.

Das S R, Hensley S E, David A, Schmidt L, Gibbs J S, Puigbo P, Ince W L, Bennick J R, Yewdell J W. 2011. Fitness costs limit influenza A virus hemagglutinin glycosylation as an immune evasion strategy. Proc. Natl. Acad. Sci. 108: E1417-E1422.

Das S R, Puigbo P, Hensley S E, Hurt D E, Bennick J R, Yewdell J W. 2010. Glycosylation focuses sequence variation in the influenza A virus H1 hemagglutinin globular domain. PLoS Pathog 6:e1001211.

Desselberger U, Nakajima K, Alfino P, Pedersen F, Haseltine W, Hannoun C, Palese P. 1978. Biochemical evidence that "new" influenza virus strains in nature may arise by recombination (reassortment). Proc. Natl. Acad. Sci. 75:3341-3345.

Hause B M, Oleson T A, Stine D L, Bey R F, Simonson R R. 2011. Genetic and antigenic characterization of recent human-like H1 (6-cluster) swine influenza virus isolates. J. Swine Health Prod. 19:268-276.

Hause B M, Oleson T A, Bey R F, Stine D L, Simonson R R. 2010. Antigenic categorization of contemporary H3N2 swine influenza virus isolates using a high-throughput serum neutralization assay. J. Vet. Diagn. Invest. 22:352-359.

Hay A J, Gregory V, Douglas A R, Lin Y P. 2001. The evolution of human influenza viruses. Philos. T. R. Soc. B. 356:1861-1870.

Hensley S E, Das S R, Gibbs J S, Bailey A L, Schmidt L M, Bennick J R, Yewdell J W. 2011. Influenza A virus hemagglutinin antibody escape promotes neuraminidase antigenic variation and drug resistance. PLoS ONE 6:e15190.

Hoffmann E, Stech J, Guan Y, Webster R G, Perez D R. 2001. Universal primer set for the full length amplification of al influenza viruses. Arch. Virol. 146:2275-2289.

Hoffmann E, Neumann G, Kawaoka Y, Hobom G, Webster R G. 2000. A DNA transfection system for generation of influenza A virus from eight plasmids. Proc. Natl. Acad. Sci. 97:6108-6113.

Karasin A I, Carman S, Olsen C W. 2006. Identification of human H1N2 and human-swine reassortant H1N2 and H1N1 influenza A viruses among pigs in Ontario, Canada (2003-2005). J. Clin. Microbiol. 44:1123-1126.

Long J, Bushnell R V, Tobin J K, Pan K, Deem M W, Nara P L, Tobin G J. 2011. Evolution of H3N2 influenza virus in a guinea pig model. PLoS ONE 6:e20130.

Lorusso A, Vincent A L, Gramer M R, Lager K M, Ciacci-Zanella J R. 2012. Contemporary epidemiology of North American lineage triple reassortant influenza A viruses in pigs. Curr. Top. Microbiol. Immunol. January 22 [epub ahead of print].

Sali A, Potterton L. 1995. Evaluation of comparative protein modeling by MODELLER." Proteins 23: 318-326.

Schild G, Oxford J, Dowdle W, Coleman M, Pereira M, Chakraverty P. 1974. Antigenic variation in current influenza A viruses: evidence for a high frequency of antigenic 'drift' for the Hong Kong virus. Bull. World Health Organ. 51:1-11.

Schulze I T. 1997. Effects of glycosylation on the properties and functions of influenza virus hemagglutinin. J. Infect. Dis. 176:S24-S28

Strengell M, Ikonen N, Ziegler T, Julkunen I. 2011. Minor changes in the hemagglutinin of influenza A (H1N1)2009 virus alter its antigenic properties. PLoS ONE 6:e25848.

Sun S, Wang Q, Zhao F, Chen W, Li Z. 2011. Glycosylation site alteration in the evolution of influenza A (H1N1) viruses. PLoS ONE 6:e22844.

Sun S, Wang Q, Zhao F, Chen W, Li Z. 2012. Prediction of biological functions on glycosylation site migrations in human influenza H1N1 viruses. PLoS ONE 7:e32119.

WHO Manual on Animal Influenza Diagnosis and Surveillance, 2002, which is entitled "WHO CDS CSR NCSi2002.5.pdf," and which may be accessed at Whqlibdoc.Who.int/hq/2002.

Tamura K, Peterson D, Peterson N, Stecher G, Nei M, and Kumar S. 2011. MEGA5: Molecular evolutionary genetics analysis using maximum likelihood, evolutionary distance, and maximum parsimony methods. Mol. Biol. Evol. 28: 2731-2739.

Vigerust D J, Ulett K B, Boyd K L, Madsen J, Hawgood S, McCullers J A. 2007. N-linked glycosylation attenuates H3N2 influenza viruses. J. Virology 81:8593-8600.

Vincent A L, Ma W, Lager K M, Gramer M R, Richt J A, Janke B H. 2009. Characterization of a newly emerged genetic cluster of H1N1 and H1N2 swine influenza virus in the United States. Virus Genes 39:176-185.

Wagner R, Wolff T, Herwig A, Pleschka S, Klenk H-D. 2000. Interdependence of hemagglutinin glycosylation and neuraminidase as regulators of influenza virus growth: a study by reverse genetics. J. Virology 74:6316-6323.

Wanzeck K, Boyd K L, McCullers J A. 2011. Glycan shielding of the influenza virus hemagglutinin contributes to immunopathology in mice. Am. J. Respir. Crit. Care Med. 183:767-773.

Wei C-J, Boyington J C, Dai K, Houser K V, Pearce M B, Kong W-P, Yang Z, Tumpey T M, Nabel G J. 2010. Cross-neutralization of 1918 and 2009 influenza viruses: role of glycans in viral evolution and vaccine design. Sci. Trans. Med. 2:24fa21. doi:10.1126/scitrans1med.3000799.

Zhou B, Donnelly M E, Scholes D T, George K S, Hatta M, Kawaoka Y, Wentworth D E. 2009. Single-reaction genomic amplification accelerates sequencing and vaccine production for classical and swine origin human influenza A viruses. J. Virology 83:10309-10313.

The invention will now be further described by way of the following non-limiting examples.

EXAMPLES

Example 1

Construction of Hyperglycosylated Swine Influenza Viruses

Materials/Methods.

Clinical samples (nasal swabs or lung tissue) were collected from pigs exhibiting influenza-like illness and were submitted for viral isolation and characterization (routine diagnostic testing). Virus isolation was performed on swine testicle (ST) cells grown in DMEM containing 5% fetal bovine serum at 37° C. with 5% $CO_2$. For viral propagation, fetal bovine serum was omitted from the DMEM. 293T and MDCK cells were propagated in DMEM containing 10% fetal bovine serum. RNA was harvested from infected cell culture harvest fluids using the 5× MagMax-96 Viral Isolation Kit (Life Technologies).

Complete viral genomes were amplified using a previously described multisegment reverse transcription PCR method (Zhou B, et al. 2009). Viral cDNA libraries were prepared using the NEBNext Fast DNA Fragmentation and Library Prep Set 4 kit according to the manufacturer's instructions (New England Biolabs) with the exception that the kit adaptors were replaced with barcoded adaptors (Ion Xpress Barcode Adaptor 1-16 Kit, Life Technologies). DNA sequencing templates were prepared using the Ion Xpress Template Kit version 2.0 (Life Technologies) and sequenced using an Ion Torrent Personal Genome Machine (Life Technologies). Contigs were assembled using SeqMan NGen software (DNAStar). Contigs encoding full length HA were identified by BLAST analysis. Full length HA DNA sequences were aligned using the ClustalW method. Phylogenetic analyses were performed using MEGA 5.0 using the neighbor joining method and tree topology was verified with 1000 bootstrap replicates (Tamura K, et al. 2011). HA gene sequences were deposited to Genbank under accession numbers JQ638655-JQ638665.

Reverse Genetics. In the context of molecular biology, "reverse genetics" is defined as the generation of virus possessing a genome derived from cloned cDNAs (for a review, see Neumann et al., J. Gen. Viral., 83:2635; 2002). In the instant study, a triple reassortant internal gene cassette (TRIG) swine influenza virus (A/swine/North Carolina/3793/08(H1N1)) was used as the template to create a TRIG swine influenza virus reverse genetics system. All eight segments were PCR amplified, digested with BsmBI and ligated into a similarly digested pHW2000 as previously described (Hoffmann E, et al. 2001). Plasmids bearing insert were identified by restriction digest and sequenced to verify identity with A/swine/North Carolina/3793/08. The HA and NA genes (SEQ ID NOs:7 & 11) from 10-0036-2 were also cloned into pHW2000 (Hoffmann et al 2000, PNAS 97(11): 6108-6113) and transfected along with plasmids bearing polymerase basic 2 (PB2), polymerase basic 1 (PB1), polymerase acid (PA), nucleoprotein (NP), matrix (M) and non-structural genes (NS) derived from A/swine/North Carolina/3793/08 to produce reverse genetics-derived 10-0036-2 (RG 10-0036-2, FIG. 1). Site directed mutagenesis was performed on the plasmid containing HA gene from 10-0036-2 to create mutants with an additional 1-5 N-linked glycosylation sites using the Quik Change II Site Directed Mutagenesis kit (Agilent Technologies) (Table 1, FIG. 2). Glycans are added to proteins at asparagine (N) residues located in the context of the N-linked glycosylation motif of N-X-S/T, where N is the amino acid asparagine, X is any amino acid and S/T is serine or threonine.

TABLE 1

Additional N-linked glycosylation sites engineered into the HA gene of RG10-0036-2 using site directed mutagenesis

| Number additional N-linked glycosylation sites | Nucleotide Change | Amino Acid Change |
|---|---|---|
| 1 | G212A | S71N |
| 2 | G212A, G270T | S71N, K90N |
| 3 | G212A, G270T, CT517-518AC | S71N, K90N, L173T |
| 4 | G212A, G270T, CT517-518AC, C859A | S71N, K90N, L173T, P287T |
| 5 | G212A, G270T, CT517-518AC, C859A, A881C | S71N, K90N, L173T, P287T, K294T |

Rescue of recombinant viruses was performed as previously described (Hoffmann E, et al. 2000). In brief, 293T and MDCK cells were co-cultured in Opti-MEM I containing 5% FBS in 6-well plates approximately $1 \times 10^6$ cells of each 293T and MDCK approximately 18 hours prior to transfection. One hundred nanograms of each of the eight plasmids were pooled in 100 μL of Opti-MEM I and combined with 100 μL Opti-MEM containing 3 μL Lipofectamine (Invitrogen) and incubated at room temperature 15 minutes before being diluted to 1 mL with Opti-MEM I and transferred to a single well of the 6-well plate. Plates were incubated at 37° C. with 5% $CO_2$ for 6 hours before the transfection mixture was replaced with Opti-MEM I. At 24 hours post transfection, 1.5 mL was transferred to a 6-well plate of confluent MDCK cells and 1.5 mL of DMEM containing 1 μg/mL of TPCK-treated trypsin was added. Viruses were harvested on day 5 post infection and their titers determined by the HA assay. The HA genes of rescued viruses were sequenced to verify the correct sequence.

Results. Genetic analysis of predicted N-linked glycosylation sites (N-X-S/T) found sites at N28, N40, N104, N142, N176, N303, N497 and N556 for virus 10-0036-2. Site directed mutagenesis was used to add an additional 1-5 N-linked glycosylation sites to the globular head portion of HA (Table 1). Following virus rescue from cell culture, mutant viruses were characterized by growth studies on ST cells. Growth studies were performed as attenuated viruses often demonstrate decreased growth rates and titers in vitro. Mutant viruses with 4 or 5 additional N-linked glycosylation sites showed such growth defects, suggesting that additional glycosylation attenuated the viruses. The attenuated viruses were next evaluated in swine to evaluate their virulence in vivo and characterize the immune response against these mutant viruses.

Example 2

Efficacy of Attenuated Swine Influenza Vaccines in Pigs

Materials & Methods. Sixty 3-week old high health pigs (confirmed SIV seronegative by IDEXX FlockChek ELISA) were separated into 4 groups of 15 in separate rooms. On day 0 (d0), pigs were inoculated intranasally with 2 mL of 6.0 $TCID_{50}$/mL virus. Group 1 was mock infected with cell culture media (DMEM). Group 2 received 10-0036-2 n+5. Group 3 received 10-0036-2 n+4 (a mutant with 4 additional glycosylation sites; similar to n+5 but lacking the mutation A881C [K294I]). Group 4 received reverse genetics created 10-0036-2 parent (no mutations). Pigs were swabbed (nasal) at day 0 and samples were run by QPCR for SIV detection to verify no active infection. Results are summarized in Table 2. For Tables 2 and 3, groups with different letters have statistically different means (P<0.05). For example, "A" is statistically different from "B", and "BC" is statistically different from "A" but not "B" or "C".

TABLE 2

Vaccination study

| Vaccination (H1N2) | Nasal Swab, Day 3 ($TCID_{50}$/mL) | Nasal Swab, Day 5 ($TCID_{50}$/mL) | Lung Titer, Day 5 ($TCID_{50}$/mL) | Lung Score | IHC Score |
|---|---|---|---|---|---|
| Neg. Con | 0.0 A | 0.0 A | 0.0 A | 0.0 A | 0.0 A |
| n + 4 mutant | 3.1 B | 2.8 B | 0.9 A | 0.0 A | 0.0 A |
| n + 5 mutant | 2.6 C | 2.7 B | 0.4 A | 0.2 A | 0.2 A |
| parent | 4.1 D | 3.2 C | 5.4 B | 1.5 B | 2.0 B |

Nasal swabs collected on days 1, 3 and 5. Five pigs from each group were euthanized at day 5 and lung samples were collected. Swabs from day 1 were analyzed by QPCR. Swabs from days 3 and 5 as well as lung samples were titrated for SIV. Lungs were sent to a University Diagnostic lab for histopathological analysis and IHC. On day 21 pigs were revaccinated as above. These results demonstrate the mutants containing 4 or 5 additionally N-linked glycosylation sites are attenuated and avirulent in swine, in agreement with the in vitro growth studies. Nasal swab titrations indicated that the virus was capable of replicating in vivo, however, absence of virus in lungs and lack of lung damage suggest replication limited to the upper respiratory tract. Mutations in other influenza genes that confer temperature sensitivity have been shown to limit infection to the upper respiratory tract and are the basis of the human live attenuated influenza vaccine FluMist™.

On day 31, pigs were challenged with a field isolate 12-1110-1 (H3N2). The results of the challenge study are summarized in Table 3. For the challenge (performed comparably to Richt et al 2006, J. Virology 80(22):11009-11018) 2mL of 4.6 TCID50/mL was delivered intranasally. Blood and nasal swabs were collected on day 31 prior to challenge. Nasal swabs were collected on days 0 and 1, and analyzed by QPCR. Nasal swabs were collected on days 3 and 5 and SIV titer determined by titration. All pigs were euthanized on day 5 and lung samples analyzed by titration. Lung samples analyzed as above.

TABLE 3

Challenge study

| H3N2 Challenge | Nasal Swab, Day 3 ($TCID_{50}$/mL) | Nasal Swab, Day 5 ($TCID_{50}$/mL) | Lung Titer, Day 5 ($TCID_{50}$/mL) | Lung Score | IHC Score |
|---|---|---|---|---|---|
| Neg. Con | 5.4 A | 5.8 A | 3.0 A | 1.6 A | 1.5 A |
| n + 4 mutant | 2.3 B | 0.7 B | 0.0 B | 0.0 B | 0.0 B |
| n + 5 mutant | 2.9 BC | 1.8 C | 0.1 B | 0.0 B | 0.0 B |
| parent | 0.5 C | 0.9 BC | 0.0 B | 0.0 B | 0.0 B |

These results demonstrate that pigs vaccinated with mutants n+4 or n+5 were protected from disease as evident by lack of virus in lungs by titration and IHC, as well as no evidence of lung lesions. Naïve (negative control) pigs were readily infected with the H3N2 challenge virus and demonstrated classical influenza disease. Pigs previously infected with the parent virus 10-0036-2 were also protected from the H3N2 challenge.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An attenuated swine influenza strain capable of providing a safe and effective immune response in a porcine animal against a virulent H3N2 swine influenza or diseases caused by H3N2 swine influenza;
   wherein the attenuated strain encodes an HA protein having five additional glycosylation sites, relative to its corresponding virulent parental strain;
   wherein the virulent parental strain encodes an HA protein having the polypeptide sequence as set forth in SEQ ID NO: 18; and
   wherein the five glycosylation sites are S71N, K90N, L173T, P287T, and K294T.

2. An immunological composition comprising the strain of claim 1.

3. The attenuated strain of claim 1, containing an HA gene encoding an HA protein having the polypeptide sequence as set forth in SEQ ID NO: 22.

4. An immunological composition comprising the strain of claim 2.

5. The attenuated strain of claim 1, encoding an HA protein having only five additional glycosylation sites, relative to its corresponding virulent parental strain.

6. An immunological composition comprising the strain of claim 5.

7. The composition of claim 6, further comprising a pharmaceutically or veterinary acceptable vehicle, diluent or excipient, and which provides a protective immune response in a porcine animal against a virulent H3N2 swine influenza challenge.

8. The composition of claim 7, further comprising at least one additional antigen associated with or derived from a porcine pathogen other than H3N2 swine influenza.

9. The composition of claim 8, wherein the at least one or more additional antigen(s) is capable of eliciting in a porcine animal an immune response against *Mycoplasma hyopneumoniae* (M. hyo), porcine circovirus 2 (PCV2), porcine reproductive and respiratory syndrome virus (PRRSV) or other pathogen capable of infecting and causing illness or susceptibility to illness in a porcine.

10. A method of vaccinating a porcine animal in need of protection against H3N2 swine influenza, comprising administering to said porcine animal the composition of claim 6, thereby vaccinating the animal.

11. The method of claim 10, wherein the porcine animal is a sow from about 3 weeks to about 6 weeks prefarrowing.

12. The method of 11, wherein the resulting piglets have a reduced morbidity and/or mortality as compared to piglets coming from unvaccinated sows.

* * * * *

SEQUENCE LISTING

```
<160> NUMBER OF SEQ ID NOS: 30

<210> SEQ ID NO 1
<211> LENGTH: 2277
<212> TYPE: DNA
<213> ORGANISM: Influenza A virus

<400> SEQUENCE: 1
atggagagaa taaaagaact aagagatctg atgtcgcagt ctcgcactcg cgagatactc      60
acaaagacca ctgtggacca tatggccata atcaaaaagt acacatcagg aaggcaagag     120
aagaaccccg cactcagaat gaagtggatg atggcaatga atacccaat tacagcagac     180 aagagaataa tggacatgat tccagagagg aatgaacaag gacaaaccct ctggagcaaa     240
acaaacgatg ctggatcgga ccgtgtgatg gtatcacccc tggccgtaac atggtggaat     300
aggaatggcc aacaacaag cacagttcac taccctaagg tatataaaac ttatttcgaa     360
aagatcgaaa ggttaaaaca tggtatcttt ggccctgtcc acttcagaaa tcaagttaaa     420
```

-continued

```
ataagaagga gggttgacac aaaccctggt catgcagatc tcagtgccaa ggaggcacag    480
gatgtgatca tggaagttgt tttcccaaat gaagtggggg caagagtact gacgtcagag    540
tcacagctga caataacaaa ggaaaagaaa gaagagctcc aggattgtaa gattgctccc    600
ctgatggtgg catacatgct agaaagagag ttggttcgca agacgaggtt tctcccggtg    660
gctggtggaa caagcagtgt ttatattgaa gtgctacact taactcaggg aacatgctgg    720
gaacaaatgt acactccagg aggagaagtg agaaatgatg atgttgacca agtttttgatt   780 atcgctgcta gaaacatagt aagaagagca gcagtgtcag cagacccatt agcatctctc   840
ttggaaatgt gccacagcac acagattgga ggaataagga tggtgacat ccttagacag     900 aacccaacgg aggaacaagc cgtagacata tgcaaggcag caatgggct gaggattagc    960 tcttctttca gctttggtgg gttcaccttc aaaagaacaa gcggatcatc agttaagaaa   1020
gaagaagaag tgctcacggg caacctccaa acactgaaaa taagagtaca tgaaggatat  1080
gaagaattca caatggtagg gagaagagca actgctattc tcagaaaagc aaccaggaga  1140
ttgatccagt aatagtaag tgggagagac gatcaatcaa ttgctgaggc aataattgta    1200
gccatggtat tttcacaaga ggattgcatg atcaaggcag ttaggggcga tctgaactt   1260 gtcaataggg caaaccagcg actgaatccc atgcaccaac tcttgaggca tttccaaaaa  1320
gatgcaaaag tgctttttcca gaactgggga attgaaccca tcgacagtgt gatgggaatg  1380
atcgggatat tgcctgatat gacccccaagc acggaaatgt cgctgagagg tataagagtc  1440
agcaaaatgg gagtagatga gtattccagc acggagagag tggtagtgag cattgaccga  1500
tttttgagag ttcgggatca acgagggaac gtactattgt cccccgaaga ggtcagcgag  1560
acacaaggaa ctgagaaatt gacaataact tattcgtcat caatgatgtg ggagatcaat  1620
ggtcctgagt cagtgctggt caacacttat caatggatca taaggaattg ggaaagcttg  1680
aaaattcaat ggtcacaaga tcccacgatg ttatacaaca aaatggaatt tgaaccattc  1740
cagtctcttg tccctaaggc aaccagaagt cgttacagtg gattcgtgag gacactgttc  1800
cagcaaatgc gggatgtgct tggaacattt gacactgtcc aaataataaa acttctcccc  1860
tttgctgctg ctccaccgga acagagtagg atacagttct cctcgctgac tgtgaatgtg  1920
agaggatcag ggctgaggat actggtaaga ggcaattctc cagtgttcaa ttacaacaaa  1980
gcaaccaaaa ggcttacaat tcttggaaaa gatgcaggtg cattgactga agatccagat  2040
gaaggcacag ctggagtgga gtctgctgtc ctgaggggat cctcatttt gggtaaagaa   2100 gacaagagat atgccccagc attaagcatc aatgaactga gcaatcttgc aaaaggagag  2160
aaggctaatg tgttaattgg gcaaggagac gtggtgttgg taatgaaacg gaaacggaac  2220
tctagcatac ttactgacag ccagacagcg accaaaagaa ttcggatggc catcaat      2277
```

<210> SEQ ID NO 2
<211> LENGTH: 759
<212> TYPE: PRT
<213> ORGANISM: Influenza A virus

<400> SEQUENCE: 2

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

```
Trp Met Met Ala Met Lys Tyr Pro Ile Thr Ala Asp Lys Arg Ile Met
     50                   55                   60
Asp Met Ile Pro Glu Arg Asn Glu Gln Gly Gln Thr Leu Trp Ser Lys
 65                   70                   75                   80
Thr Asn Asp Ala Gly Ser Asp Arg Val Met Val Ser Pro Leu Ala Val
                      85                   90                   95
Thr Trp Trp Asn Arg Asn Gly Pro Thr Thr Ser Thr Val His Tyr Pro
                 100                  105                  110
Lys Val Tyr Lys Thr Tyr Phe Glu Lys Ile Glu Arg Leu Lys His Gly
             115                  120                  125
Ile Phe Gly Pro Val His Phe Arg Asn Gln Val Lys Ile Arg Arg Arg
     130                  135                  140
Val Asp Thr Asn Pro Gly His Ala Asp Leu Ser Ala Lys Glu Ala Gln
145                  150                  155                  160
Asp Val Ile Met Glu Val Val Phe Pro Asn Glu Val Gly Ala Arg Val
                 165                  170                  175
Leu Thr Ser Glu Ser Gln Leu Thr Ile Thr Lys Glu Lys Lys Glu Glu
                 180                  185                  190
Leu Gln Asp Cys Lys Ile Ala Pro Leu Met Val Ala Tyr Met Leu Glu
             195                  200                  205
Arg Glu Leu Val Arg Lys Thr Arg Phe Leu Pro Val Ala Gly Gly Thr
     210                  215                  220
Ser Ser Val Tyr Ile Glu Val Leu His Leu Thr Gln Gly Thr Cys Trp
225                  230                  235                  240
Glu Gln Met Tyr Thr Pro Gly Gly Glu Val Arg Asn Asp Asp Val Asp
                 245                  250                  255
Gln Ser Leu Ile Ile Ala Ala Arg Asn Ile Val Arg Arg Ala Ala Val
                 260                  265                  270
Ser Ala Asp Pro Leu Ala Ser Leu Leu Glu Met Cys His Ser Thr Gln
             275                  280                  285
Ile Gly Gly Ile Arg Met Val Asp Ile Leu Arg Gln Asn Pro Thr Glu
     290                  295                  300
Glu Gln Ala Val Asp Ile Cys Lys Ala Ala Met Gly Leu Arg Ile Ser
305                  310                  315                  320
Ser Ser Phe Ser Phe Gly Gly Phe Thr Phe Lys Arg Thr Ser Gly Ser
                 325                  330                  335
Ser Val Lys Lys Glu Glu Glu Val Leu Thr Gly Asn Leu Gln Thr Leu
                 340                  345                  350
Lys Ile Arg Val His Glu Gly Tyr Glu Glu Phe Thr Met Val Gly Arg
             355                  360                  365
Arg Ala Thr Ala Ile Leu Arg Lys Ala Thr Arg Arg Leu Ile Gln Leu
     370                  375                  380
Ile Val Ser Gly Arg Asp Asp Gln Ser Ile Ala Glu Ala Ile Ile Val
385                  390                  395                  400
Ala Met Val Phe Ser Gln Glu Asp Cys Met Ile Lys Ala Val Arg Gly
                 405                  410                  415
Asp Leu Asn Phe Val Asn Arg Ala Asn Gln Arg Leu Asn Pro Met His
                 420                  425                  430
Gln Leu Leu Arg His Phe Gln Lys Asp Ala Lys Val Leu Phe Gln Asn
             435                  440                  445
Trp Gly Ile Glu Pro Ile Asp Ser Val Met Gly Met Ile Gly Ile Leu
     450                  455                  460
```

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val
            485                 490                 495

Ser Ile Asp Arg Phe Leu Arg Val Arg Asp Gln Arg Gly Asn Val Leu
                500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Ser Leu
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Thr Arg Ser Arg Tyr
                580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
        610                 615                 620

Pro Pro Glu Gln Ser Arg Ile Gln Phe Ser Ser Leu Thr Val Asn Val
625                 630                 635                 640

Arg Gly Ser Gly Leu Arg Ile Leu Val Arg Gly Asn Ser Pro Val Phe
                645                 650                 655

Asn Tyr Asn Lys Ala Thr Lys Arg Leu Thr Ile Leu Gly Lys Asp Ala
                660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asn Ser Ser Ile Leu Thr Asp Ser Gln Thr Ala Thr Lys
                740                 745                 750

Arg Ile Arg Met Ala Ile Asn
        755

<210> SEQ ID NO 3
<211> LENGTH: 2271
<212> TYPE: DNA
<213> ORGANISM: Influenza A virus

<400> SEQUENCE: 3
atggatgtca acccgactct acttttccta aaggttccag cgcaaaatgc cataagcacc    60
acattcccdt atactggaga tcctccatac agccatggaa caggaacagg atacaccatg    120
gacacagtca acagaacaca ccagtattca gaaaagggga atggacgac aaacacagag     180 actggggcac cccagctcaa cccgattgat ggaccactac ccgatgataa tgaaccaagt    240
gggtatgcac aaacagactg tgtcctggag gccatggctt ccttgaaga tcccacccca    300 gggatatttg agaattcatg ccttgaaaca atgaaattg tccaacaaac aagggtggat    360
aaactaactc aaggtcgcca gactatgat tggacattaa acagaaatca accggcagca    420

| | |
|---|---|
| actgcattgg ccaacaccat agaagttttt agatcaaacg gtctaacagc taatgagtca | 480 |
| ggaaggctaa tagatttcct aaaggatgta atggaatcaa tggataagga ggaaatagag | 540 |
| ataacaacac attttcaaag aaaaaggaga gtaagagaca acatgaccaa gaagatggtc | 600 |
| acacaaagaa caatagggaa gaaaaaacaa aaattgaata agagaagtta tctaataaga | 660 |
| gcactgacat tgaatacgat gaccaaagat gcagagagag gcaagttaaa aaggagggct | 720 |
| atcgcaacac ctgggatgca gattagaggg ttcgtgtact tgttgagac tttagctaga | 780 |
| agcatctgcg aaaagcttga acagtccgga ctcccagtag ggggcaatga aaagaaagcc | 840 |
| aaattggcaa atgttgtgag aaagatgatg actaattcac aagacacaga gctttctttc | 900 |
| acaatcactg gagataacac taaatggaat gaaaaccaga tcctcgaat gttcctggcg | 960 |
| atgatcacat acattaccag aaatcaaccc gagtggttca gaaacatact gagtatggca | 1020 |
| ccaataatgt tctcaaacaa aatggcaaga ctaggaaaag ggtacatgtt cgagagtaaa | 1080 |
| agaatgaagc tccgaacaca ggtaccagca gaaatgctag caagcattga tcttaagtat | 1140 |
| ttcaatgaat caacaaggaa gaaaattgag aaaataaggc ctctcctaat agatggcaca | 1200 |
| gcatcattga gccctgggat gatgatgggc atgttcaaca tgctaagtac ggttttggga | 1260 |
| gtctcaatac tgaatcttgg acaaaagaaa tacaccagga caacatactg gtgggatgga | 1320 |
| ctccaatcct cagacgattt tgccctcata gtaaatgcac caaatcatga gggaatacaa | 1380 |
| gcaggagtgg atagattcta caggacctgc aagttagtag gatcaacat gagcaaaaag | 1440 |
| aagtcctata taaataagac tgggacattt gaattcacaa gctttttta tcgctatggg | 1500 |
| tttgtagcta attttagcat ggagctgccc agttttggga tgtctggaat aaacgaatca | 1560 |
| gctgatatga gcatcggagt aacagtgata aagaacaaca tgataaataa tgatcttgga | 1620 |
| cctgcaacag cccagatggc cctccagttg ttcatcaaag actacagata cacatataga | 1680 |
| tgccatagag gggacacaca aatccagacg agaagatcat tcgagctaaa gagcctgtgg | 1740 |
| aatcaaactc aatcaaaggc aggattatta gtatctgatg gaggaccaaa tttatacaat | 1800 |
| atccggaatc ttcacattcc tgaagtctgc ttaaatgggg agctaatgga tgaggattat | 1860 |
| cggggaagac tttgtaatcc cctgaatccc tttgtcagcc ataaagagat tgattctgta | 1920 |
| aacagtgctg tggtgatgcc agcccatggt ccagccaaaa gtatggagta tgatgccgtt | 1980 |
| gcaactacac actcctggat tcccaagagg aaccgctcta ttctcaacac aagccaaagg | 2040 |
| ggaattcttg aggatgaaca gatgtaccag aagtgctgca acctgttcga aaattttc | 2100 |
| cctagtagtt catacagaag accagttgga atttctagca tggtggaggc catggtgtct | 2160 |
| agggcccgga ttgatgccag gattgacttc gagtctggac ggattaagaa agaagagttc | 2220 |
| tctgagatca tgaagatctg ttccaccatt gaagaactca gacggcaaaa g | 2271 |

<210> SEQ ID NO 4
<211> LENGTH: 757
<212> TYPE: PRT
<213> ORGANISM: Influenza A virus

<400> SEQUENCE: 4

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

```
Tyr Ser Glu Lys Gly Lys Trp Thr Thr Asn Thr Glu Thr Gly Ala Pro
     50              55                  60

Gln Leu Asn Pro Ile Asp Gly Pro Leu Pro Asp Asp Asn Glu Pro Ser
65              70                  75                  80

Gly Tyr Ala Gln Thr Asp Cys Val Leu Glu Ala Met Ala Phe Leu Glu
             85                  90                  95

Glu Ser His Pro Gly Ile Phe Glu Asn Ser Cys Leu Glu Thr Met Glu
            100                 105                 110

Ile Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
        130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Val Arg
            180                 185                 190

Asp Asn Met Thr Lys Lys Met Val Thr Gln Arg Thr Ile Gly Lys Lys
            195                 200                 205

Lys Gln Lys Leu Asn Lys Arg Ser Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Val
        355                 360                 365

Pro Ala Glu Met Leu Ala Ser Ile Asp Leu Lys Tyr Phe Asn Glu Ser
370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
            405                 410                 415

Thr Val Leu Gly Val Ser Ile Leu Asn Leu Gly Gln Lys Lys Tyr Thr
            420                 425                 430

Arg Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
```

```
                465                 470                 475                 480
            Lys Ser Tyr Ile Asn Lys Thr Gly Thr Phe Glu Phe Thr Ser Phe Phe
                            485                 490                 495
            Tyr Arg Tyr Gly Phe Val Ala Asn Phe Ser Met Glu Leu Pro Ser Phe
                            500                 505                 510
            Gly Val Ser Gly Ile Asn Glu Ser Ala Asp Met Ser Ile Gly Val Thr
                            515                 520                 525
            Val Ile Lys Asn Asn Met Ile Asn Asn Asp Leu Gly Pro Ala Thr Ala
                            530                 535                 540
            Gln Met Ala Leu Gln Leu Phe Ile Lys Asp Tyr Arg Tyr Thr Tyr Arg
            545                 550                 555                 560
            Cys His Arg Gly Asp Thr Gln Ile Gln Thr Arg Arg Ser Phe Glu Leu
                            565                 570                 575
            Lys Ser Leu Trp Asn Gln Thr Gln Ser Lys Ala Gly Leu Leu Val Ser
                            580                 585                 590
            Asp Gly Gly Pro Asn Leu Tyr Asn Ile Arg Asn Leu His Ile Pro Glu
                            595                 600                 605
            Val Cys Leu Lys Trp Glu Leu Met Asp Glu Asp Tyr Arg Gly Arg Leu
            610                 615                 620
            Cys Asn Pro Leu Asn Pro Phe Val Ser His Lys Glu Ile Asp Ser Val
            625                 630                 635                 640
            Asn Ser Ala Val Val Met Pro Ala His Gly Pro Ala Lys Ser Met Glu
                            645                 650                 655
            Tyr Asp Ala Val Ala Thr Thr His Ser Trp Ile Pro Lys Arg Asn Arg
                            660                 665                 670
            Ser Ile Leu Asn Thr Ser Gln Arg Gly Ile Leu Glu Asp Glu Gln Met
                            675                 680                 685
            Tyr Gln Lys Cys Cys Asn Leu Phe Glu Lys Phe Phe Pro Ser Ser Ser
                            690                 695                 700
            Tyr Arg Arg Pro Val Gly Ile Ser Ser Met Val Glu Ala Met Val Ser
            705                 710                 715                 720
            Arg Ala Arg Ile Asp Ala Arg Ile Asp Phe Glu Ser Gly Arg Ile Lys
                            725                 730                 735
            Lys Glu Glu Phe Ser Glu Ile Met Lys Ile Cys Ser Thr Ile Glu Glu
                            740                 745                 750
            Leu Arg Arg Gln Lys
                    755

<210> SEQ ID NO 5
<211> LENGTH: 2148
<212> TYPE: DNA
<213> ORGANISM: Influenza A virus

<400> SEQUENCE: 5
atggaagact tgtgcgaca atgcttcaat ccaatgatcg tcgagcttgc ggaaaaggca      60
atgaaagaat atgagaaga tccgaaaatt gaaactaaca aattcgctgc aatatgcaca     120
cacttggaag tatgtttcat gtattcagat ttccatttca ttgacgagcg gggtgaatca     180
atcattgtag aatctggtga tccaaatgca ttactgaagc accgatttga gataattgaa     240
ggacgagacc ggaccatggc ctggacagta gtgaacagta tctgcaacac cacagggta     300 gagaagccta aatttcttcc ggatttatac gactacaaag aaaatcggtt cattgaaatt     360
ggagtgcaca caagggaggt ccacatatac tacctagaga agccaacaa atataaaatcc    420 gagaagacac acattcacat tttttcattc actggagagg agatggccac caaagcagac     480
```

```
tacacccttg atgaagaaag cagggcaaga atcaaaacca ggcttttcac cataagacaa      540
gaaatggcaa gtagggg tct atgggattcc tttcgtcagt ccgaaagagg cgaggagaca     600
attgaagaaa gatttgaaat tacaggaacc atgcgcagac ttgccgacca aagtctccca     660
ccgaacttct ccagtcttga aaactttaga gcttatgtag atgggttcga accaaacggc     720
tgcattgagg gcaagctttc tcaaatgtca aagaagtga gcgcccaaat gaacccttc      780 ttgaagacaa caccacgccc tctaaaattg cctgatgggc ctccttgctc tcagcggtca     840
aagttcttgc tgatggatgc tctgaaacta gtattgaag acccgagtca tgaaggagaa      900
ggaataccac tatatgatgc aatcaagtgc atgaagacat tttttggctg aaagaaccc     960 aacataatca accacatga aaaggcata aaccccaatt acctactggc ttggaagcag      1020
gtgctagcag agctccaaga cattgaaaat gaagagaaga tcccaaagac aaagaacatg     1080
aggagaacaa gccaattgaa gtgggcactc ggtgagaata tggcaccaga gaaagtagat     1140
tttgatgact gcaaagatgt tggtgatctt aaacagtatg acagcgacga gccagagccc     1200
agatctctag caagttgggt ccaaaatgaa ttcaacaagg catgtgaatt gaccgattca     1260
agctggatag aacttgatga gataggagaa gatattgcac cgattgaaca catcgcaagt     1320
atgaggagga actatttac agcagaagtg tcccattgta gggctacgga atacataatg      1380
aagggagtgt acataaacac ggctttgctt aatgcatctt gtgcagccat ggatgacttt      1440
cagctgatcc caatgataag caaatgcagg accaagaag gaagacgaaa acaaatctg     1500 tatgggttca ttataaaagg aaggtcccat ctgaggaatg atactgacgt ggtgaacttt      1560
gtaagcatgg agttctccct caccgacccg agactggagc cacacaaatg ggaaaaatac     1620
tgtgttcttg aaataggaga catgctcctg aggactgcga taggccaagt gtcgaggccc     1680
atgttcttat atgtgagaac caatggaacc tccaagatca gatgaaatg gggcatggaa     1740 atgaggcgct gccttcttca atctcttcag cagattgaga gcatgattga ggctgagtct     1800
tctgtaaaag agaaagacat gaccaaggaa ttttttgaaa acaaatcgga aacatggcca     1860
attggagaat cacccaaagg agtgaggaa ggctctattg ggaaagtgtg caggaccta      1920 ctggcaaaat ctgtattcaa cagtctatac gcgtctccac aacttgaggg attttcggct      1980
gaatcgagaa agttgcttct cattgttcag gcacttaggg acaacctgga acctggaacc     2040
ttcgatcttg gggctata tgaagcaatc gaggagtgcc tgattaatga tccctgggtt       2100
ttgcttaatg catcttggtt caactccttc ctcacacatg cactgaaa                  2148
```

<210> SEQ ID NO 6
<211> LENGTH: 716
<212> TYPE: PRT
<213> ORGANISM: Influenza A virus

<400> SEQUENCE: 6

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asp Glu Arg Gly Glu Ser Ile Ile Val Glu
        50                  55                  60

Ser Gly Asp Pro Asn Ala Leu Leu Lys His Arg Phe Glu Ile Ile Glu
65                  70                  75                  80
```

```
Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Ser Ala Gln
                245                 250                 255

Ile Glu Pro Phe Leu Lys Thr Thr Pro Arg Pro Leu Lys Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Ile Lys Pro His Glu Lys Gly Ile Asn Pro Asn Tyr Leu Leu
                325                 330                 335

Ala Trp Lys Gln Val Leu Ala Glu Leu Gln Asp Ile Glu Asn Glu Glu
            340                 345                 350

Lys Ile Pro Lys Thr Lys Asn Met Arg Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Ile
            420                 425                 430

Ala Pro Ile Glu His Ile Ala Ser Met Arg Arg Asn Tyr Phe Thr Ala
    435                 440                 445

Glu Val Ser His Cys Arg Ala Thr Glu Tyr Ile Met Lys Gly Val Tyr
450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495
```

```
Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715

<210> SEQ ID NO 7
<211> LENGTH: 1692
<212> TYPE: DNA
<213> ORGANISM: Influenza A virus

<400> SEQUENCE: 7
atgaaggcaa tactagtagt cctgctatat acatttacaa ccgcaaatgc cgacacatta      60
tgcataggtt atcatgcgaa caattcaact gacaccgtag acacagtgct agaaaaaaat     120
gtaacagtaa cacactctgt caaccttcta gaaaacaggc ataatgggaa actatgtaaa     180
ctaagagggg tagctccatt gcatttgggt aaatgtaaca ttgctggctg gctcctggga     240
aatccagagt gtgagtcaat ctccaaagca agctcatggt cctacattgt ggaaacatct     300
aattcagaca atgggacgtg ttacccagga gatttcatca attatgagga gctaagagag     360
cagttgagct cagtgtcatc atttgaaaga tttgagatat cccccatgac aagttcatgg     420
cccaatcatg acgcaacag aggtgtgacg gcagcatgtc ctcacgctgg acaaatagc     480 ttctacaaaa atttaatatg gctggtcaaa aaggaaatt catacccaaa gatcaacaaa     540
tcctacatta acaacaaaga gaaagaagtt ctcgtgctat gggccataca tcatccacct     600
accaatgccg accaacaaag cctctaccaa atgcagatg cctatgtttt tgtggggtca     660
tcaagataca gcaggaagtt cgagccagaa atagcaacaa gacccaaggt gagagaccaa     720
gcagggagaa tgaactatta ctggacattg gtagagcctg agacaagat aacattcgaa     780 gcaactggaa atcagtggt accgagatat gccttcgcat tgaaaagaaa ttctggatct     840
ggtattatca tttcagatac atcagtccac gattgtgata cgacttgtca gacacccaat     900
```

```
ggtgctataa acaccagcct cccatttcaa aatatacatc cagtcacaat tggagaatgt    960
ccaaaatatg taaaaagtac taaactgaga atggccacag gattaaggaa tatcccgtct   1020
attcaatcta gaggcctgtt tggggccatt gctggcttta ttgaaggggg ctggacagga   1080
atgatagacg gatggtacgg ttaccaccat caaaatgagc agggatcagg atatgcagcc   1140
gacctgaaaa gcacacagaa tgccattgac gggatcacta acaaggtaaa ttctgttatt   1200
gaaaagatga acacacaatt cacagcagta ggtaaagagt tcagccactt ggaaagaaga   1260
atagagaatt taaataaaaa ggttgatgat ggttttctag atatttggac ttacaatgcc   1320
gaactgttgg ttctgttgga gaatgaaaga actttggatt accacgattc aaatgtgaaa   1380
aacttatatg aaaaagtaag aagccaacta aaaaacaatg ccaaagaaat tggaaatggc   1440
tgctttgaat tttaccacaa atgtgatgac acgtgtatgg aaagcgtcaa aaatgggact   1500
tatgattacc caaaatactc agaggaagca aaactaaaca gagaggaaat agatggggta   1560
aagttggaat caacaagggt ttaccaaatt ttggcgatct attcaacggt cgccagttca   1620
ttggtactgg tagtctccct gggggcaatc agtttctgga tgtgctctaa tgggtcgcta   1680
cagtgcagaa ta                                                       1692
```

<210> SEQ ID NO 8
<211> LENGTH: 564
<212> TYPE: PRT
<213> ORGANISM: Influenza A virus

<400> SEQUENCE: 8

```
Met Lys Ala Ile Leu Val Val Leu Leu Tyr Thr Phe Thr Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Arg His Asn Gly Lys Leu Cys Lys Leu Arg Gly Val
    50                  55                  60

Ala Pro Leu His Leu Gly Lys Cys Asn Ile Ala Gly Trp Leu Leu Gly
65                  70                  75                  80

Asn Pro Glu Cys Glu Ser Ile Ser Lys Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Met Thr Ser Ser Trp Pro Asn His Asp
    130                 135                 140

Thr Asn Arg Gly Val Thr Ala Ala Cys Pro His Ala Gly Thr Asn Ser
145                 150                 155                 160

Phe Tyr Lys Asn Leu Ile Trp Leu Val Lys Lys Gly Asn Ser Tyr Pro
                165                 170                 175

Lys Ile Asn Lys Ser Tyr Ile Asn Asn Lys Glu Lys Glu Val Leu Val
            180                 185                 190

Leu Trp Ala Ile His His Pro Pro Thr Asn Ala Asp Gln Gln Ser Leu
        195                 200                 205

Tyr Gln Asn Ala Asp Ala Tyr Val Phe Val Gly Ser Ser Arg Tyr Ser
    210                 215                 220
```

```
Arg Lys Phe Glu Pro Glu Ile Ala Thr Arg Pro Lys Val Arg Asp Gln
225                 230                 235                 240

Ala Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Leu Lys Arg Asn Ser Gly Ser Gly Ile Ile Ile Ser Asp Thr Ser
        275                 280                 285

Val His Asp Cys Asp Thr Thr Cys Gln Thr Pro Asn Gly Ala Ile Asn
    290                 295                 300

Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Ser His
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asp Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Val Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile

<210> SEQ ID NO 9
<211> LENGTH: 1512
<212> TYPE: DNA
<213> ORGANISM: Influenza A virus

<400> SEQUENCE: 9
atgagtgaca tcgaagccat ggcgtctcaa ggcaccaaac gatcatatga acaaatggag      60
actggtggtg aacgccagga tgccacagaa atcagagcat ctgtcggaag aatgattggt     120
ggaatcggga aattctacat ccaaatgtgc actgaactca aactcagtga ctatgaggga     180
```

-continued

```
cgactaatcc aaaatagcat aacaatagag agaatggtgc tctctgcttt tgatgagaga    240
agaaataaat acctagaaga gcatcccagt gctgggaaag accctaagaa aactggagga    300
cccatatata gaagagtaga cggaaagtgg atgagagaac tcattcttta tgacaaagaa    360
gaaataagga gagtttggcg ccaggcaaac aatggtgatg atgcaacagc tggtcttact    420
catatcatga tttggcattc caatctgaat gatgccacgt accagagaac aagagcactt    480
gttcgcaccg gaatggatcc cagaatgtgc tctctaatgc aaggttcaac acttcccaga    540
aggtctggag cagcaggtgc tgcagtgaaa ggagttggaa caataacaat ggaattaatc    600
agaatgatca aacgggggat caatgaccga aatttctgga gaggtgaaaa tggaagaagg    660
acaaggattg catatgaaag aatgtgcaat attctcaaag gaaaatttca gacagctgcc    720
caaagggcaa tgatggatca agtgagagaa agtcggaacc cagggaacgc tgagattgaa    780
gatctcattt tcctggcacg gtcagcactt atcctaaggg gatcagttgc acataagtct    840
tgcctgcctg cttgcgtgta tgggcttgca gtggcaagtg ggcatgactt tgaaagggaa    900
gggtattcgc tggtcgggat agacccattt aaattactcc agaacagtca agtgttcagc    960
ctggtaagac caaatgaaaa cccagctcac aagagtcaat tagtgtggat ggcatgccac   1020
tctgctgcat ttgaggatct aagggtctca agtttcataa gagggaagaa agtgattcca   1080
aggggaaagc tttccacaag aggggttcag attgcttcaa atgagaatgt ggaagccatg   1140
gattccaata ccttagagct gagaagcaga tactgggcta taaggaccag aagtggagga   1200
aatactaatc aacagaaagc atccgcaggc cagatcagtg tgcaacctac attctcagtg   1260
caacggaatc tccctttgga aagagcaacc gttatggcag ctttcagcgg aaacaatgaa   1320
ggacggacat ccgatatgcg gacagaaatt ataaggatga tggaaaatgc aaaaccagaa   1380
gatttgtcct tccaggggcg ggagtcttc gagctctcgg acgaaaaggc aacgagcccg   1440
atcgtgcctt cctttgacat gagtaatgaa gggtcttatt tcttcggaga caatgcagag   1500
gagtatgaca gt                                                         1512
```

```
<210> SEQ ID NO 10
<211> LENGTH: 504
<212> TYPE: PRT
<213> ORGANISM: Influenza A virus

<400> SEQUENCE: 10

Met Ser Asp Ile Glu Ala Met Ala Ser Gln Gly Thr Lys Arg Ser Tyr
1               5                   10                  15

Glu Gln Met Glu Thr Gly Gly Glu Arg Gln Asp Ala Thr Glu Ile Arg
            20                  25                  30

Ala Ser Val Gly Arg Met Ile Gly Gly Ile Gly Lys Phe Tyr Ile Gln
        35                  40                  45

Met Cys Thr Glu Leu Lys Leu Ser Asp Tyr Glu Gly Arg Leu Ile Gln
    50                  55                  60

Asn Ser Ile Thr Ile Glu Arg Met Val Leu Ser Ala Phe Asp Glu Arg
65                  70                  75                  80

Arg Asn Lys Tyr Leu Glu Glu His Pro Ser Ala Gly Lys Asp Pro Lys
                85                  90                  95

Lys Thr Gly Gly Pro Ile Tyr Arg Arg Val Asp Gly Lys Trp Met Arg
            100                 105                 110

Glu Leu Ile Leu Tyr Asp Lys Glu Glu Ile Arg Arg Val Trp Arg Gln
        115                 120                 125

Ala Asn Asn Gly Asp Asp Ala Thr Ala Gly Leu Thr His Ile Met Ile
```

-continued

```
    130                 135                 140

Trp His Ser Asn Leu Asn Asp Ala Thr Tyr Gln Arg Thr Arg Ala Leu
145                 150                 155                 160

Val Arg Thr Gly Met Asp Pro Arg Met Cys Ser Leu Met Gln Gly Ser
                165                 170                 175

Thr Leu Pro Arg Arg Ser Gly Ala Ala Gly Ala Ala Val Lys Gly Val
            180                 185                 190

Gly Thr Ile Thr Met Glu Leu Ile Arg Met Ile Lys Arg Gly Ile Asn
        195                 200                 205

Asp Arg Asn Phe Trp Arg Gly Glu Asn Gly Arg Arg Thr Arg Ile Ala
    210                 215                 220

Tyr Glu Arg Met Cys Asn Ile Leu Lys Gly Lys Phe Gln Thr Ala Ala
225                 230                 235                 240

Gln Arg Ala Met Met Asp Gln Val Arg Glu Ser Arg Asn Pro Gly Asn
                245                 250                 255

Ala Glu Ile Glu Asp Leu Ile Phe Leu Ala Arg Ser Ala Leu Ile Leu
            260                 265                 270

Arg Gly Ser Val Ala His Lys Ser Cys Leu Pro Ala Cys Val Tyr Gly
        275                 280                 285

Leu Ala Val Ala Ser Gly His Asp Phe Glu Arg Glu Gly Tyr Ser Leu
    290                 295                 300

Val Gly Ile Asp Pro Phe Lys Leu Leu Gln Asn Ser Gln Val Phe Ser
305                 310                 315                 320

Leu Val Arg Pro Asn Glu Asn Pro Ala His Lys Ser Gln Leu Val Trp
                325                 330                 335

Met Ala Cys His Ser Ala Ala Phe Glu Asp Leu Arg Val Ser Ser Phe
            340                 345                 350

Ile Arg Gly Lys Lys Val Ile Pro Arg Gly Lys Leu Ser Thr Arg Gly
        355                 360                 365

Val Gln Ile Ala Ser Asn Glu Asn Val Glu Ala Met Asp Ser Asn Thr
    370                 375                 380

Leu Glu Leu Arg Ser Arg Tyr Trp Ala Ile Arg Thr Arg Ser Gly Gly
385                 390                 395                 400

Asn Thr Asn Gln Gln Lys Ala Ser Ala Gly Gln Ile Ser Val Gln Pro
                405                 410                 415

Thr Phe Ser Val Gln Arg Asn Leu Pro Phe Glu Arg Ala Thr Val Met
            420                 425                 430

Ala Ala Phe Ser Gly Asn Asn Glu Gly Arg Thr Ser Asp Met Arg Thr
        435                 440                 445

Glu Ile Ile Arg Met Met Glu Asn Ala Lys Pro Glu Asp Leu Ser Phe
    450                 455                 460

Gln Gly Arg Gly Val Phe Glu Leu Ser Asp Glu Lys Ala Thr Ser Pro
465                 470                 475                 480

Ile Val Pro Ser Phe Asp Met Ser Asn Glu Gly Ser Tyr Phe Phe Gly
                485                 490                 495

Asp Asn Ala Glu Glu Tyr Asp Ser
            500

<210> SEQ ID NO 11
<211> LENGTH: 1407
<212> TYPE: DNA
<213> ORGANISM: Influenza A virus

<400> SEQUENCE: 11
```

-continued

```
atgaatacaa atcaaagaat aataaccatt gggacagttt gtctgatagt tggaataatt      60
agtctattgt tacagatagg aaacatggtt tcgttatgga tcagccattc aattcagact     120
gaagggaaaa atcatactga gatgtgcaat caaaatgtca ttacatatgt aaataacaca     180
tgggtgaacc gaacttatgt aaacattagc aataccaaaa ttgttaatgt acaggacgtg     240
gtttcagtaa tattaaccgg caattcctct ctctgcccaa taagtgggtg ggctatatac     300
agcaaagaca atagcataag gattggttct aaaggggaca tttttgtcat aagagaacca     360
ttcatttcat gctctcactt ggaatgcaga actttttttc tgacccaagg cgctttgctg     420
aatgacaagc attctaatgg aaccgtcaag gacaggagtc cctatagaac tttaatgagc     480
tgtcccatcg gtgaagctcc atctccatat aactcaaggt tcgaatcagt tgcttggtca     540
gcaagtgcat gccatgatgg gatgggatgg ctaacaatcg gaatctccgg tccagataat     600
ggagcagtag ctgttttaaa atacaacggt ataataacag atacaataaa aagttggaga     660
aacaaaatat taagaacaca agagtcagaa tgtgtttgta tgaacggttc ttgttttact     720
gtattaactg atggcccaag caatgggcaa gcatcgtaca aaatattcaa gatggaaaaa     780
ggaaaaataa ttaaatcaat tgagctggat gcacccaatt accactatga ggaatgctcc     840
tgttatcctg atgcaggcaa agtaatgtgt gtttgcagag acaactggca tgcctcgaac     900
cggccatggg tctctttcga tcagaatctt aattatcaaa tagggtacat atgcagtggg     960
gttttcggtg ataacccgcg ttctaatgat ggaaagggca attgtggccc agtacattct    1020
aatggagcaa atggagtgaa aggattctca tataaatatg gtaatggtgt ttggatagga    1080
aggactaaaa gtatcaactc cagaagtgga tttgaaatga tttgggatcc aaatgggtgg    1140
actggaactg atagtagttt ctctatgaag caggatatta tagcattaac tgattggtca    1200
ggatacagtg gaagttttgt ccaacatcct gaattaacag gaatgaattg cataaggccc    1260
tgtttctggg tagaattaat cagagggcaa cccaaggaaa acaccatctg ggctagcgga    1320
agcagcatct ctttctgtgg tgtaaatggt gaaaccgcaa gctggtcatg gccagacgga    1380
gctgatctgc cattcaccat tgacaag                                        1407
```

```

<210> SEQ ID NO 12
<211> LENGTH: 469
<212> TYPE: PRT
<213> ORGANISM: Influenza A virus

<400> SEQUENCE: 12

Met Asn Thr Asn Gln Arg Ile Ile Thr Ile Gly Thr Val Cys Leu Ile
1               5                   10                  15

Val Gly Ile Ile Ser Leu Leu Leu Gln Ile Gly Asn Met Val Ser Leu
            20                  25                  30

Trp Ile Ser His Ser Ile Gln Thr Glu Gly Lys Asn His Thr Glu Met
        35                  40                  45

Cys Asn Gln Asn Val Ile Thr Tyr Val Asn Asn Thr Trp Val Asn Arg
    50                  55                  60

Thr Tyr Val Asn Ile Ser Asn Thr Lys Ile Val Asn Val Gln Asp Val
65                  70                  75                  80

Val Ser Val Ile Leu Thr Gly Asn Ser Ser Leu Cys Pro Ile Ser Gly
                85                  90                  95

Trp Ala Ile Tyr Ser Lys Asp Asn Ser Ile Arg Ile Gly Ser Lys Gly
            100                 105                 110

Asp Ile Phe Val Ile Arg Glu Pro Phe Ile Ser Cys Ser His Leu Glu
        115                 120                 125
```

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Lys Ile Leu
210                 215                 220

Arg Thr Gln Glu Ser Glu Cys Val Cys Met Asn Gly Ser Cys Phe Thr
225                 230                 235                 240

Val Leu Thr Asp Gly Pro Ser Asn Gly Gln Ala Ser Tyr Lys Ile Phe
                245                 250                 255

Lys Met Glu Lys Gly Lys Ile Ile Lys Ser Ile Glu Leu Asp Ala Pro
            260                 265                 270

Asn Tyr His Tyr Glu Glu Cys Ser Cys Tyr Pro Asp Ala Gly Lys Val
        275                 280                 285

Met Cys Val Cys Arg Asp Asn Trp His Ala Ser Asn Arg Pro Trp Val
290                 295                 300

Ser Phe Asp Gln Asn Leu Asn Tyr Gln Ile Gly Tyr Ile Cys Ser Gly
305                 310                 315                 320

Val Phe Gly Asp Asn Pro Arg Ser Asn Asp Gly Lys Gly Asn Cys Gly
                325                 330                 335

Pro Val His Ser Asn Gly Ala Asn Gly Val Lys Gly Phe Ser Tyr Lys
            340                 345                 350

Tyr Gly Asn Gly Val Trp Ile Gly Arg Thr Lys Ser Ile Asn Ser Arg
        355                 360                 365

Ser Gly Phe Glu Met Ile Trp Asp Pro Asn Gly Trp Thr Gly Thr Asp
370                 375                 380

Ser Ser Phe Ser Met Lys Gln Asp Ile Ile Ala Leu Thr Asp Trp Ser
385                 390                 395                 400

Gly Tyr Ser Gly Ser Phe Val Gln His Pro Glu Leu Thr Gly Met Asn
                405                 410                 415

Cys Ile Arg Pro Cys Phe Trp Val Glu Leu Ile Arg Gly Gln Pro Lys
            420                 425                 430

Glu Asn Thr Ile Trp Ala Ser Gly Ser Ser Ile Ser Phe Cys Gly Val
        435                 440                 445

Asn Gly Glu Thr Ala Ser Trp Ser Trp Pro Asp Gly Ala Asp Leu Pro
450                 455                 460

Phe Thr Ile Asp Lys
465

<210> SEQ ID NO 13
<211> LENGTH: 756
<212> TYPE: DNA
<213> ORGANISM: Influenza A virus

<400> SEQUENCE: 13
atgagtcttc taaccgaggt cgaaacgtat gttctctcta tcgtcccgtc aggccccctc    60
aaagccgaga tagcacagag gctcgaagac gttttttgcag ggaaaaacac cgatcttgag   120

```
gctctcatgg aatggctaaa gacaagacca atcctgtcac ctctgactaa agggatttta    180
gggtttgtgt tcacgctcac cgtgcccagt gagcgaggac tgcagcgtag acgttttgtc    240
cagaatgccc tcaatgggaa tggtgaccca acaacatgg acaaggcggt aaaactgtac     300
aggaaactaa aagggaaat aacattccat ggggccaagg aagtagcgct cagttactct     360
gctggtgcac ttgccagttg catgggcctc atatacaaca gaatggggac tgtcgccact    420
gaggtggcat ttggtctggt atgcgcaacc tgtgaacaaa ttgctgattc tcagcatcga    480
tctcatagac aaatggtgac aacaaccaat ccactaatca ggcacgagaa cagaatggta    540
atagccagca aacagctaa ggccatggaa caaatggctg atcaagtga acaagcagca     600 gaggctatgg aggttgccag tcaggctaga caaatggtac aggcaatgag aacaattggg    660
actcacccta gttccagcac tggtctaaaa gatgatcttc ttgaaaattt acaggcctat    720
cagaaacgga tgggagtgca aatgcaacga ttcaag                              756
```

<210> SEQ ID NO 14
<211> LENGTH: 252
<212> TYPE: PRT
<213> ORGANISM: Influenza A virus

<400> SEQUENCE: 14

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Ala Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Ile Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Thr Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 15
<211> LENGTH: 657
<212> TYPE: DNA
<213> ORGANISM: Influenza A virus

<400> SEQUENCE: 15

| | | | | | |
|---|---|---|---|---|---|
| atggactcca | atactgtgtc | aagctttcag | gtagactgtt | tcctttggca | catccgcaaa | 60 |
| cgatttgcag | acaatggatt | gggtgatgcc | ccattccttg | atcggctccg | ccgagatcaa | 120 |
| aagtccctaa | aaggaagggg | caacacccct | agcctagaca | tcgaaacagc | cactcttgtt | 180 |
| gggaaacaaa | ttgttgagtg | gattttgaaa | gaggaatcca | gcgatatact | taagatgacc | 240 |
| attgcatctg | tgcctacttc | gcgctaccta | gctgacatga | ccctcgagga | aatgtcacga | 300 |
| gactggttca | tgctaatgcc | taggcaaaag | ataataggcc | ctctttgtgt | gcgagtggac | 360 |
| caggcgatca | tggaaaagaa | catcactctg | aaagcgaact | tcagtgtgat | ctttaaccga | 420 |
| ttagagactt | tgatactact | aagggctttc | actgaggagg | gagcaatcgt | tggagaaatt | 480 |
| tcaccattac | cttatcttcc | aggacatact | aatgaggatg | tcaaaaatgc | agttggggtc | 540 |
| ctcatcggag | gcttgaatgg | aatggtaac | acggttcgag | gctctgaaaa | tctacagaga | 600 |
| ttcgcttgga | gaaaccataa | tgaggatggg | agatcttcac | tacctccaga | acagaaa | 657 |

<210> SEQ ID NO 16
<211> LENGTH: 219
<212> TYPE: PRT
<213> ORGANISM: Influenza A virus

<400> SEQUENCE: 16

Met Asp Ser Asn Thr Val Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Asn
        35                  40                  45

Thr Leu Ser Leu Asp Ile Glu Thr Ala Thr Leu Val Gly Lys Gln Ile
    50                  55                  60

Val Glu Trp Ile Leu Lys Glu Glu Ser Ser Asp Ile Leu Lys Met Thr
65                  70                  75                  80

Ile Ala Ser Val Pro Thr Ser Arg Tyr Leu Ala Asp Met Thr Leu Glu
                85                  90                  95

Glu Met Ser Arg Asp Trp Phe Met Leu Met Pro Arg Gln Lys Ile Ile
            100                 105                 110

Gly Pro Leu Cys Val Arg Val Asp Gln Ala Ile Met Glu Lys Asn Ile
        115                 120                 125

Ile Leu Lys Ala Asn Phe Ser Val Ile Phe Asn Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Tyr Leu Pro Gly His Thr Asn Glu Asp Val Lys Asn
                165                 170                 175

Ala Val Gly Val Leu Ile Gly Gly Leu Glu Trp Asn Gly Asn Thr Val
            180                 185                 190

Arg Gly Ser Glu Asn Leu Gln Arg Phe Ala Trp Arg Asn His Asn Glu
        195                 200                 205

Asp Gly Arg Ser Ser Leu Pro Pro Glu Gln Lys
    210                 215

<210> SEQ ID NO 17
<211> LENGTH: 1695
<212> TYPE: DNA
<213> ORGANISM: Influenza A virus

<400> SEQUENCE: 17

| | | | | | |
|---|---|---|---|---|---|
| atgaaagtaa | aactaatggt | tctgttatgt | acatttacag | ctacatatgc | agacacaata | 60 |
| tgtgtaggct | accatgccaa | caactcaact | gacactgttg | acacagtact | tgagaagaat | 120 |
| gtgacagtga | cacactctgt | caacctactt | gaggacagcc | acaatggaaa | actatgtcta | 180 |
| ctaaaaggaa | tagctccact | acaattgggt | agttgcagcg | ttgccggatg | gatcttagga | 240 |
| aacccagagt | gcgaattgct | gatttccaag | gaatcttggt | cctacattgt | agaaacacca | 300 |
| aatcctgaga | atggaacatg | ttaccagggg | tatttcacag | actatgaaga | actgagggag | 360 |
| caattgagtt | cagtatcttc | atttaagagg | ttcgaaatat | tccccaaaga | gagctcatgg | 420 |
| cccaaccaca | ccgtaaccgg | agtgtcatca | tcatgctccc | ataacgggaa | aagcagcttc | 480 |
| tacagaaatt | tgctatggct | gacggtgaag | aacggtctgt | acccaaacct | gagcaagtcc | 540 |
| tatacaaaca | aaaaggagaa | agaagtcctt | gtactatggg | gtgttcatca | cccatctaac | 600 |
| atagggacc | aaagggccct | ctatcataca | gaaaatgctt | atgtctctgt | agtgtcttca | 660 |
| cattatagca | gaagattcac | cccagaaata | gccaaaagac | ccaaggtgag | aaatcaggaa | 720 |
| ggaagaatca | actactactg | gaccctgcta | gaacccgggg | atacaataat | atttgaggca | 780 |
| aatggaaatc | taatagcacc | aaggtatgcc | ttcgaactga | gtaagggttt | tggatcagga | 840 |
| atcatcacat | caaatgcacc | aatgggtgaa | tgtaatgcaa | agtgtcaaac | acctcaggga | 900 |
| gctataaaca | gcagtcttcc | tttccagaat | gtacacccag | taacaatagg | agagtgccca | 960 |
| aagtatgtca | aaagtgcaaa | attaaggatg | gttacaggac | taaggaacac | ccatccatt | 1020 |
| caatccagag | gtttgtttgg | agccattgcc | ggtttcattg | aaggagggtg | gactggaatg | 1080 |
| gtagatggtt | ggtatggtta | tcaccatcag | aatgagcaag | gatctgggta | tgctgcagac | 1140 |
| caacaaagca | cacaaaatgc | cattaatggg | attacaaaca | aggtgaattc | tgtgattgaa | 1200 |
| aaaatgaaca | ctcaattcac | agctgtgggc | aaagaattca | acaaactgga | agaagaatg | 1260 |
| gaaaacttaa | ataaaaaggt | tgatgatggg | tttctagaca | tttggacata | taatgcagaa | 1320 |
| ttgttagttc | tactggaaaa | tgaaaggact | ttggatttcc | atgactccaa | cgtgaagaat | 1380 |
| ctgtatgaga | aagtaaaaag | ccaattaaaa | aataatgcca | agaaatagg | aaacgggtgt | 1440 |
| tttgaattct | atcataagtg | taacgatgaa | tgcatggaga | gtgtgaaaaa | tggaacttat | 1500 |
| gactatccaa | atattccga | agaatcaaag | ttaaacaggg | agaaaattga | tggagtgaaa | 1560 |
| ttggaatcaa | tgggagtcta | taatatcctg | gcgatctact | caacagtcgc | cagttcccta | 1620 |
| gttcttttag | tctccctggg | ggcaatcagc | ttctggatgt | gttccaatgg | gtctttacag | 1680 |
| tgtagaatat | gcatc | | | | | 1695 |

<210> SEQ ID NO 18
<211> LENGTH: 565
<212> TYPE: PRT
<213> ORGANISM: Influenza A virus

<400> SEQUENCE: 18

Met Lys Val Lys Leu Met Val Leu Leu Cys Thr Phe Thr Ala Thr Tyr
1 5 10 15

Ala Asp Thr Ile Cys Val Gly Tyr His Ala Asn Asn Ser Thr Asp Thr
20 25 30

```
Val Asp Thr Val Leu Glu Lys Asn Val Thr Val Thr His Ser Val Asn
    35                  40                  45

Leu Leu Glu Asp Ser His Asn Gly Lys Leu Cys Leu Leu Lys Gly Ile
50                  55                  60

Ala Pro Leu Gln Leu Gly Ser Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
                100                 105                 110

Thr Asp Tyr Glu Glu Leu Arg Glu Gln Leu Ser Ser Val Ser Ser Phe
            115                 120                 125

Lys Arg Phe Glu Ile Phe Pro Lys Glu Ser Ser Trp Pro Asn His Thr
        130                 135                 140

Val Thr Gly Val Ser Ser Cys Ser His Asn Gly Lys Ser Ser Phe
145                 150                 155                 160

Tyr Arg Asn Leu Leu Trp Leu Thr Val Lys Asn Gly Leu Tyr Pro Asn
                165                 170                 175

Leu Ser Lys Ser Tyr Thr Asn Lys Lys Glu Lys Glu Val Leu Val Leu
                180                 185                 190

Trp Gly Val His His Pro Ser Asn Ile Gly Asp Gln Arg Ala Leu Tyr
            195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asn Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Glu
            260                 265                 270

Leu Ser Lys Gly Phe Gly Ser Gly Ile Ile Thr Ser Asn Ala Pro Met
        275                 280                 285

Gly Glu Cys Asn Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Lys Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Gln Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445
```

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Asn
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 19
<211> LENGTH: 1407
<212> TYPE: DNA
<213> ORGANISM: Influenza A virus

<400> SEQUENCE: 19
atgaatccaa atcaaaagat aataacgatt ggctctgttt ctcttactat tgccacaatg      60
tgcttcctta tgcaaattgc catcctggta actaatgtaa cattgcactt caatcaatat     120
gaatgcaact accccccaaa caaccaagta atactgtgtg aaccaacaat aatagaaaga     180
aacataacag agatagtgta tctgaccaac accaccatag aaggaaat atgccccaaa       240 ctagcagaat acagaaattg gtcaaagccg caatgtaaaa ttacagggtt tgcaccttt      300 tccaaggaca attcgattag ctttctgct ggtggggaca tttgggtgac gagagaacct      360
tatgtgtcat gcgatcctga taagtgttat cagtttgccc ttggacaagg aacaacatta    420
aacaacaggc attcaaatga cacagtacat gataggaccc cttatcgaac cctattgatg    480
aatgagttgg gtattccatt ccatttgggg accaaacaag tgtgcatagc atggtccagc    540
tcaagttgtc atgatggaaa agcatggctt cacgtttgta ttactgggca tgataaaaat    600
gcaactgcta gcttcattta caatgggagg cttgtagata tattggttc atggtccaaa    660 aaaatactca ggacacagga gtcggaatgt gtttgcatca atggaacttg tacagtagta    720
atgactgatg ggagtgcttc aggaatagct gacactaaaa tattattcat tgaagagggg    780
aaaatcgttc atattagccy attgttagga agtgctcagc atgtagagga gtgctcctgt    840 tatcccgat atcctggtgt cagatgcatc tgtagagaca actggaaagg ttccaataga    900
cccgtcgtag atataaatgt aaaggattat agcattgttt ccagttatgt gtgctcagga    960
cttgttggag atacacccag aaaagacgac agatccagca gtagcgattg tctgaatcct   1020
aacaatgagg aagggggca tggagtgaaa ggctgggcct tgatgatgg aaatgatgtg     1080 tggatgggaa gaacaatcaa cgagacgtta cgctcaggtt atgaaacctt caaagtcatt   1140
gaaggctggt ccaaacctaa ttccaaattg cagataaata gcaagtcat agttgaaaga    1200 ggtgataggt ccggttattc tggcattttc tctgttgaag caaaagctg tatcaatcgg    1260 tgcttttatg tggagttgat aagaggaagg aaacaggaaa ctgcagtatg gtggacgtca    1320
aacagtattt ttgtgttttg tggcacctca ggtacatatg aacaggctc atggcctgat    1380 ggggcgaaca tcaatctcat gcctgta                                        1407
```

```
<210> SEQ ID NO 20
<211> LENGTH: 469
<212> TYPE: PRT
<213> ORGANISM: Influenza A virus
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid

<400> SEQUENCE: 20

Met Asn Pro Asn Gln Lys Ile Ile Thr Ile Gly Ser Val Ser Leu Thr
1               5                   10                  15

Ile Ala Thr Met Cys Phe Leu Met Gln Ile Ala Ile Leu Val Thr Asn
            20                  25                  30

Val Thr Leu His Phe Asn Gln Tyr Glu Cys Asn Tyr Pro Pro Asn Asn
        35                  40                  45

Gln Val Ile Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
145                 150                 155                 160

Asn Glu Leu Gly Ile Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Ile Thr Gly His Asp Xaa Asn Ala Thr Ala Ser Phe Ile Tyr Asn
        195                 200                 205

Gly Arg Leu Val Asp Ser Ile Gly Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Ile Ala Asp Thr Lys Ile Leu Phe
                245                 250                 255

Ile Glu Glu Gly Lys Ile Val His Ile Ser Xaa Leu Leu Gly Ser Ala
            260                 265                 270

Gln His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Val Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asp Asp Arg Ser Ser Ser Ser Asp
                325                 330                 335
```

Cys Leu Asn Pro Asn Asn Glu Glu Gly Gly His Gly Val Lys Gly Trp
              340                 345                 350

Ala Phe Asp Asp Gly Asn Asp Val Trp Met Gly Arg Thr Ile Asn Glu
          355                 360                 365

Thr Leu Arg Ser Gly Tyr Glu Thr Phe Lys Val Ile Glu Gly Trp Ser
      370                 375                 380

Lys Pro Asn Ser Lys Leu Gln Ile Asn Arg Gln Val Ile Val Glu Arg
385                 390                 395                 400

Gly Asp Arg Ser Gly Tyr Ser Gly Ile Phe Ser Val Glu Gly Lys Ser
              405                 410                 415

Cys Ile Asn Arg Cys Phe Tyr Val Glu Leu Ile Arg Gly Arg Lys Gln
          420                 425                 430

Glu Thr Ala Val Trp Trp Thr Ser Asn Ser Ile Val Val Phe Cys Gly
      435                 440                 445

Thr Ser Gly Thr Tyr Gly Thr Gly Ser Trp Pro Asp Gly Ala Asn Ile
    450                 455                 460

Asn Leu Met Pro Val
465

<210> SEQ ID NO 21
<211> LENGTH: 1695
<212> TYPE: DNA
<213> ORGANISM: Artificial Sequence
<220> FEATURE:
<223> OTHER INFORMATION: HA gene of Influenza 10-0036-2 (n+5, relative
      to parent)

<400> SEQUENCE: 21
atgaaagtaa aactaatggt tctgttatgt acatttacag ctacatatgc agacacaata      60
tgtgtaggct accatgccaa caactcaact gacactgttg acacagtact tgagaagaat     120
gtgacagtga cacactctgt caacctactt gaggacagcc acaatggaaa actatgtcta     180
ctaaaaggaa tagctccact acaattgggt aattgcagcg ttgccggatg gatcttagga     240
aacccagagt gcgaattgct gatttccaat gaatcttggt cctacattgt agaaacacca     300
aatcctgaga atggaacatg ttacccaggg tatttcacag actatgaaga actgagggag     360
caattgagtt cagtatcttc atttaagagg ttcgaaatat ccccaagaga gctcatgg      420 cccaaccaca ccgtaaccgg agtgtcatca tcatgctccc ataacgggaa aagcagcttc     480
tacagaaatt tgctatggct gacggtgaag aacggtacgt acccaaacct gagcaagtcc     540
tatacaaaca aaaggagaa agaagtcctt gtactatggg gtgttcatca cccatctaac     600
ataggggacc aaagggccct ctatcataca gaaaatgctt atgtctctgt agtgtcttca     660
cattatagca agattcac cccagaaata gccaaaagac ccaaggtgag aaatcaggaa     720
ggaagaatca actactactg gacctgcta gaacccgggg atacaataat atttgaggca     780
aatggaaatc taatagcacc aaggtatgcc ttcgaactga gtaagggttt tggatcagga     840
atcatcacat caaatgcaac aatgggtgaa tgtaatgcaa cgtgtcaaac acctcaggga     900
gctataaaca gcagtcttcc tttccagaat gtacacccag taacaatagg agagtgccca     960
aagtatgtca aaagtgcaaa attaaggatg gttacggac taaggaacac ccatccatt    1020 caatccagag gtttgtttgg agccattgcc ggtttcattg aaggagggtg gactggaatg    1080
gtagatggtt ggtatggtta tcaccatcag aatgagcaag atctgggta tgctgcagac    1140 caacaaagca cacaaaatgc cattaatggg attacaaaca aggtgaattc tgtgattgaa    1200

```
aaaatgaaca ctcaattcac agctgtgggc aaagaattca caaactgga agaagaatg    1260 gaaaacttaa ataaaaaggt tgatgatggg tttctagaca tttggacata taatgcagaa    1320
ttgttagttc tactggaaaa tgaaaggact ttggatttcc atgactccaa cgtgaagaat    1380
ctgtatgaga aagtaaaaag ccaattaaaa aataatgcca agaaatagg aaacgggtgt     1440 tttgaattct atcataagtg taacgatgaa tgcatggaga gtgtgaaaaa tggaacttat    1500
gactatccaa atattccga agaatcaaag ttaaacaggg agaaaattga tggagtgaaa    1560
ttggaatcaa tgggagtcta ataatcctg gcgatctact caacagtcgc cagttcccta     1620
gttcttttag tctccctggg ggcaatcagc ttctggatgt gttccaatgg gtctttacag    1680
tgtagaatat gcatc                                                     1695
```

<210> SEQ ID NO 22
<211> LENGTH: 565
<212> TYPE: PRT
<213> ORGANISM: Artificial Sequence
<220> FEATURE:
<223> OTHER INFORMATION: HA predicted AA of Influenza 10-0036-2 (n+5, relative to parent)

<400> SEQUENCE: 22

```
Met Lys Val Lys Leu Met Val Leu Leu Cys Thr Phe Thr Ala Thr Tyr
1               5                   10                  15

Ala Asp Thr Ile Cys Val Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Asn Glu Ser Trp Ser Tyr Ile
                85                  90                  95

Val Glu Thr Pro Asn Pro Glu Asn Gly Thr Cys Tyr Pro Gly Tyr Phe
            100                 105                 110

Thr Asp Tyr Glu Glu Leu Arg Glu Gln Leu Ser Ser Val Ser Ser Phe
        115                 120                 125

Lys Arg Phe Glu Ile Phe Pro Lys Glu Ser Ser Trp Pro Asn His Thr
    130                 135                 140

Val Thr Gly Val Ser Ser Ser Cys Ser His Asn Gly Lys Ser Ser Phe
145                 150                 155                 160

Tyr Arg Asn Leu Leu Trp Leu Thr Val Lys Asn Gly Thr Tyr Pro Asn
                165                 170                 175

Leu Ser Lys Ser Tyr Thr Asn Lys Lys Glu Lys Glu Val Leu Val Leu
            180                 185                 190

Trp Gly Val His His Pro Ser Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asn Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Glu
            260                 265                 270
```

Leu Ser Lys Gly Phe Gly Ser Gly Ile Ile Thr Ser Asn Ala Thr Met
          275                 280                 285
Gly Glu Cys Asn Ala Thr Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Lys Ser Ala Lys Leu Arg Met Val Thr Gly Leu Arg Asn
                325                 330                 335
Thr Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Gln Ser Thr
    370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Asn
        515                 520                 525
Ile Leu Ala Ile Tyr Ser Thr Val Ala Ser Ser Leu Val Leu Leu Val
    530                 535                 540
Ser Leu Gly Ala Ile Ser Phe Trp Met Cys Ser Asn Gly Ser Leu Gln
545                 550                 555                 560
Cys Arg Ile Cys Ile
            565

<210> SEQ ID NO 23
<211> LENGTH: 1695
<212> TYPE: DNA
<213> ORGANISM: Artificial Sequence
<220> FEATURE:
<223> OTHER INFORMATION: HA gene of Influenza 10-0036-2 (n+4, relative
      to parent)

<400> SEQUENCE: 23
atgaaagtaa aactaatggt tctgttatgt acatttacag ctacatatgc agacacaata      60
tgtgtaggct accatgccaa caactcaact gacactgttg acacagtact tgagaagaat     120
gtgacagtga cacactctgt caacctactt gaggacagcc acaatggaaa actatgtcta     180
ctaaaaggaa tagctccact acaattgggg aattgcagcg ttgccggatg gatcttagga     240
aacccagagt gcgaattgct gatttccaat gaatcttggt cctacattgt agaaacacca     300

```
aatcctgaga atggaacatg ttacccaggg tatttcacag actatgaaga actgag

```
Thr Asp Tyr Glu Glu Leu Arg Glu Gln Leu Ser Ser Val Ser Ser Phe
        115                 120                 125

Lys Arg Phe Glu Ile Phe Pro Lys Glu Ser Ser Trp Pro Asn His Thr
    130                 135                 140

Val Thr Gly Val Ser Ser Cys Ser His Asn Gly Lys Ser Ser Phe
145                 150                 155                 160

Tyr Arg Asn Leu Leu Trp Leu Thr Val Lys Asn Gly Thr Tyr Pro Asn
                165                 170                 175

Leu Ser Lys Ser Tyr Thr Asn Lys Lys Glu Lys Glu Val Leu Val Leu
                180                 185                 190

Trp Gly Val His His Pro Ser Asn Ile Gly Asp Gln Arg Ala Leu Tyr
                195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asn Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Glu
                260                 265                 270

Leu Ser Lys Gly Phe Gly Ser Gly Ile Ile Thr Ser Asn Ala Thr Met
    275                 280                 285

Gly Glu Cys Asn Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Lys Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
    355                 360                 365

His Gln Asn Glu Gln Gly Ser Gly Tyr Ala Ala Asp Gln Gln Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
    435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Asn
    515                 520                 525
```

```
Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 25
<211> LENGTH: 1695
<212> TYPE: DNA
<213> ORGANISM: Artificial Sequence
<220> FEATURE:
<223> OTHER INFORMATION: HA gene of Influenza 10-0036-2 (n+3, relative
      to parent)

<400> SEQUENCE: 25
atgaaagtaa aactaatggt tctgttatgt acatttacag ctacatatgc agacacaata     60
tgtgtaggct accatgccaa caactcaact gacactgttg acacagtact tgagaagaat    120
gtgacagtga cacactctgt caacctactt gaggacagcc acaatggaaa actatgtcta    180
ctaaaaggaa tagctccact acaattgggt aattgcagcg ttgccggatg gatcttagga    240
aacccagagt gcgaattgct gatttccaat gaatcttggt cctacattgt agaaacacca    300
aatcctgaga atggaacatg ttacccaggg tatttcacag actatgaaga actgagggag    360
caattgagtt cagtatcttc atttaagagg ttcgaaatat tccccaaaga gagctcatgg    420
cccaaccaca ccgtaaccgg agtgtcatca tcatgctccc ataacgggaa aagcagcttc    480
tacagaaatt tgctatggct gacggtgaag aacggtacgt acccaaacct gagcaagtcc    540
tatacaaaca aaaaggagaa agaagtcctt gtactatggg gtgttcatca cccatctaac    600
ataggggacc aaagggccct ctatcataca gaaaatgctt atgtctctgt agtgtcttca    660
cattatagca gaagattcac cccagaaata gccaaaagac ccaaggtgag aaatcaggaa    720
ggaagaatca actactactg gaccctgcta gaacccgggg atacaataat atttgaggca    780
aatggaaatc taatagcacc aaggtatgcc ttcgaactga gtaagggttt tggatcagga    840
atcatcacat caaatgcacc aatgggtgaa tgtaatgcaa agtgtcaaac acctcaggga    900
gctataaaca gcagtcttcc tttccagaat gtacacccag taacaatagg agagtgccca    960
aagtatgtca aaagtgcaaa attaaggatg gttacaggac taaggaacac cccatccatt   1020
caatccagag gtttgtttgg agccattgcc ggtttcattg aaggagggtg gactggaatg   1080
gtagatggtt ggtatggtta tcaccatcag aatgagcaag gatctgggta tgctgcagac   1140
caacaaagca cacaaaatgc cattaatggg attacaaaca aggtgaattc tgtgattgaa   1200
aaaatgaaca ctcaattcac agctgtgggc aaagaattca acaaactgga aagaagaatg   1260
gaaaacttaa ataaaaaggt tgatgatggg tttctagaca tttggacata taatgcagaa   1320
ttgttagttc tactggaaaa tgaaaggact ttggatttcc atgactccaa cgtgaagaat   1380
ctgtatgaga aagtaaaaag ccaattaaaa aataatgcca aagaaatagg aaacgggtgt   1440
tttgaattct atcataagtg taacgatgaa tgcatggaga gtgtgaaaaa tggaacttat   1500
gactatccaa aatattccga agaatcaaag ttaaacaggg agaaaattga tggagtgaaa   1560
ttggaatcaa tgggagtcta taatatcctg gcgatctact caacagtcgc cagttcccta   1620
gttcttttag tctccctggg ggcaatcagc ttctggatgt gttccaatgg gtctttacag   1680
tgtagaatat gcatc                                                     1695
```

```
<210> SEQ ID NO 26
<211> LENGTH: 565
<212> TYPE: PRT
<213> ORGANISM: Artificial Sequence
<220> FEATURE:
<223> OTHER INFORMATION: HA predicted AA of Influenza 10-0036-2 (n+3,
      relative to parent)

<400> SEQUENCE: 26

Met Lys Val Lys Leu Met Val Leu Leu Cys Thr Phe Thr Ala Thr Tyr
1               5                   10                  15

Ala Asp Thr Ile Cys Val Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Asn Glu Ser Trp Ser Tyr Ile
                85                  90                  95

Val Glu Thr Pro Asn Pro Glu Asn Gly Thr Cys Tyr Pro Gly Tyr Phe
            100                 105                 110

Thr Asp Tyr Glu Glu Leu Arg Glu Gln Leu Ser Ser Val Ser Ser Phe
        115                 120                 125

Lys Arg Phe Glu Ile Phe Pro Lys Glu Ser Ser Trp Pro Asn His Thr
    130                 135                 140

Val Thr Gly Val Ser Ser Ser Cys Ser His Asn Gly Lys Ser Ser Phe
145                 150                 155                 160

Tyr Arg Asn Leu Leu Trp Leu Thr Val Lys Asn Gly Thr Tyr Pro Asn
                165                 170                 175

Leu Ser Lys Ser Tyr Thr Asn Lys Lys Glu Lys Glu Val Leu Val Leu
            180                 185                 190

Trp Gly Val His His Pro Ser Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asn Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Glu
            260                 265                 270

Leu Ser Lys Gly Phe Gly Ser Gly Ile Ile Thr Ser Asn Ala Pro Met
        275                 280                 285

Gly Glu Cys Asn Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Lys Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365
```

His Gln Asn Glu Gln Gly Ser Gly Tyr Ala Ala Asp Gln Gln Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
            405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
            485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Asn
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 27
<211> LENGTH: 1695
<212> TYPE: DNA
<213> ORGANISM: Artificial Sequence
<220> FEATURE:
<223> OTHER INFORMATION: HA gene of Influenza 10-0036-2 (n+2, relative
      to parent)

<400> SEQUENCE: 27
atgaaagtaa aactaatggt tctgttatgt acatttacag ctacatatgc agacacaata      60
tgtgtaggct accatgccaa caactcaact gacactgttg acacagtact tgagaagaat    120
gtgacagtga cacactctgt caacctactt gaggacagcc acaatggaaa actatgtcta    180
ctaaaaggaa tagctccact acaattgggt aattgcagcg ttgccggatg gatcttagga    240
aacccagagt gcgaattgct gatttccaat gaatcttggt cctacattgt agaaacacca    300
aatcctgaga atggaacatg ttaccccagg tatttcacag actatgaaga actgagggag    360
caattgagtt cagtatcttc atttaagagg ttcgaaatat tccccaaaga gagctcatgg    420
cccaaccaca ccgtaaccgg agtgtcatca tcatgctccc ataacgggaa aagcagcttc    480
tacagaaatt tgctatggct gacggtgaag aacggtctgt acccaaacct gagcaagtcc    540
tatacaaaca aaaaggagaa agaagtcctt gtactatggg gtgttcatca cccatctaac    600
ataggggacc aaagggccct ctatcataca gaaaatgctt atgtctctgt agtgtcttca    660
cattatagca gaagattcac cccagaaata gccaaaagac caaaggtgag aaatcaggaa    720
ggaagaatca actactactg gaccctgcta gaacccgggg atacaataat atttgaggca    780
aatggaaatc taatagcacc aaggtatgcc ttcgaactga gtaagggttt tggatcagga    840
atcatcacat caaatgcacc aatgggtgaa tgtaatgcaa agtgtcaaac acctcaggga    900

```
gctataaaca gcagtcttcc tttccagaat gtacacccag taacaatagg agagtgccca    960
aagtatgtca aaagtgcaaa attaaggatg gttacaggac taaggaacac cccatccatt   1020
caatccagag gtttgtttgg agccattgcc ggtttcattg aaggagggtg gactggaatg   1080
gtagatggtt ggtatggtta tcaccatcag aatgagcaag gatctgggta tgctgcagac   1140
caacaaagca cacaaaatgc cattaatggg attacaaaca aggtgaattc tgtgattgaa   1200
aaaatgaaca ctcaattcac agctgtgggc aaagaattca caaactgga agaagaatg    1260 gaaaacttaa ataaaaggt tgatgatggg tttctagaca tttggacata taatgcagaa   1320
ttgttagttc tactggaaaa tgaaaggact ttggatttcc atgactccaa cgtgaagaat   1380
ctgtatgaga aagtaaaaag ccaattaaaa aataatgcca agaaatagg aacgggtgt    1440 tttgaattct atcataagtg taacgatgaa tgcatggaga gtgtgaaaaa tggaacttat   1500
gactatccaa atattccga agaatcaaag ttaaacaggg agaaaattga tggagtgaaa   1560
ttggaatcaa tgggagtcta taatatcctg gcgatctact caacagtcgc cagttcccta   1620
gttcttttag tctccctggg ggcaatcagc ttctggatgt gttccaatgg gtctttacag   1680
tgtagaatat gcatc                                                    1695
```

<210> SEQ ID NO 28
<211> LENGTH: 565
<212> TYPE: PRT
<213> ORGANISM: Artificial Sequence
<220> FEATURE:
<223> OTHER INFORMATION: HA predicted AA of Influenza 10-0036-2 (n+2, relative to parent)

<400> SEQUENCE: 28

```
Met Lys Val Lys Leu Met Val Leu Leu Cys Thr Phe Thr Ala

His Thr Glu Asn Ala Tyr Val Ser Val Val Ser Ser His Tyr Ser Arg
    210                 215                 220
Arg Phe Thr Pro Glu Ile Ala Lys Arg Pro Lys Val Arg Asn Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Glu
                260                 265                 270
Leu Ser Lys Gly Phe Gly Ser Gly Ile Ile Thr Ser Asn Ala Pro Met
            275                 280                 285
Gly Glu Cys Asn Ala Lys Cys Gln Thr Pro Gln Gly Ala Ile Asn Ser
290                 295                 300
Ser Leu Pro Phe Gln Asn Val His Pro Val Thr Ile Gly Glu Cys Pro
305                 310                 315                 320
Lys Tyr Val Lys Ser Ala Lys Leu Arg Met Val Thr Gly Leu Arg Asn
                325                 330                 335
Thr Pro Ser Ile Gln Ser Arg Gly Leu Phe Gly Ala Ile Ala Gly Phe
                340                 345                 350
Ile Glu Gly Gly Trp Thr Gly Met Val Asp Gly Trp Tyr Gly Tyr His
            355                 360                 365
His Gln Asn Glu Gln Gly Ser Gly Tyr Ala Ala Asp Gln Gln Ser Thr
        370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Asn
        515                 520                 525
Ile Leu Ala Ile Tyr Ser Thr Val Ala Ser Ser Leu Val Leu Leu Val
530                 535                 540
Ser Leu Gly Ala Ile Ser Phe Trp Met Cys Ser Asn Gly Ser Leu Gln
545                 550                 555                 560
Cys Arg Ile Cys Ile
            565

<210> SEQ ID NO 29
<211> LENGTH: 1695
<212> TYPE: DNA
<213> ORGANISM: Artificial Sequence
<220> FEATURE:
<223> OTHER INFORMATION: HA gene of Influenza 10-0036-2 (n+1, relative
      to parent)

<400> SEQUENCE: 29

```
atgaaagtaa aactaatggt tctgttatgt acatttacag ctacatatgc agacacaata      60
tgtgtaggct accatgccaa caactcaact gacactgttg acacagtact tgagaagaat     120
gtgacagtga cacactctgt caacctactt gaggacagcc acaatggaaa actatgtcta     180
ctaaaaggaa tagctccact acaattgggg agttgcagcg ttgccggatg gatcttagga     240
aacccagagt gcgaattgct gatttccaat gaatcttggt cctacattgt agaaacacca     300
aatcctgaga atggaacatg ttacccaggg tatttcacag actatgaaga actgagggag     360
caattgagtt cagtatcttc atttaagagg ttcgaaatat ccccaaagga gagctcatgg     420
cccaaccaca ccgtaaccgg agtgtcatca tcatgctccc ataacgggaa aagcagcttc     480
tacagaaatt tgctatggct gacggtgaag aacggtctgt acccaaacct gagcaagtcc     540
tatacaaaca aaaaggagaa agaagtcctt gtactatggg gtgttcatca cccatctaac     600
atagggacc aaagggccct ctatcataca gaaaatgctt atgtctctgt agtgtcttca     660
cattatagca agagattcac cccagaaata gccaaaagac ccaaggtgag aaatcaggaa     720
ggaagaatca actactactg gacctgcta gaacccgggg atacaataat atttgaggca     780
aatggaaatc taatagcacc aaggtatgcc ttcgaactga gtaaggggttt tggatcagga     840
atcatcacat caaatgcacc aatgggtgaa tgtaatgcaa agtgtcaaac acctcaggga     900
gctataaaca gcagtcttcc tttccagaat gtacacccag taacaatagg agagtgccca     960
aagtatgtca aagtgcaaaa attaaggatg gttacaggac taaggaacac cccatccatt    1020
caatccagag gtttgtttgg agccattgcc ggtttcattg aaggagggtg gactggaatg    1080
gtagatggtt ggtatggtta tcaccatcag aatgagcaag gatctgggta tgctgcagac    1140
caacaaagca cacaaaatgc cattaatggg attacaaaca aggtgaattc tgtgattgaa    1200
aaaatgaaca ctcaattcac agctgtgggc aaagaattca caaaactgga agaagaatg    1260
gaaaacttaa ataaaaaggt tgatgatggg tttctagaca tttggacata taatgcagaa    1320
ttgttagttc tactggaaaa tgaaaggact ttggatttcc atgactccaa cgtgaagaat    1380
ctgtatgaga agtaaaaaag ccaattaaaa aataatgcca agaaatagg aaacgggtgt    1440
tttgaattct atcataagtg taacgatgaa tgcatggaga gtgtgaaaaa tggaacttat    1500
gactatccaa atattccgaa gaatcaaag ttaaacaggg agaaaattga tggagtgaaa    1560
ttggaatcaa tgggagtcta ataatcctg cgatctact caacagtcgc cagttcccta    1620
gttcttttag tctccctggg ggcaatcagc ttctggatgt gttccaatgg gtctttacag    1680
tgtagaatat gcatc                                                    1695
```

<210> SEQ ID NO 30
<211> LENGTH: 565
<212> TYPE: PRT
<213> ORGANISM: Artificial Sequence
<220> FEATURE:
<223> OTHER INFORMATION: HA predicted AA of Influenza 10-0036-2 (n+1, relative to parent)

<400> SEQUENCE: 30

Met Lys Val Lys Leu Met Val Leu Leu Cys Thr Phe Thr Ala Thr Tyr
1               5                   10                  15

Ala Asp Thr Ile Cys Val Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

```
Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Thr Asp Tyr Glu Glu Leu Arg Glu Gln Leu Ser Ser Val Ser Ser Phe
            115                 120                 125

Lys Arg Phe Glu Ile Phe Pro Lys Glu Ser Ser Trp Pro Asn His Thr
130                 135                 140

Val Thr Gly Val Ser Ser Cys Ser His Asn Gly Lys Ser Ser Phe
145                 150                 155                 160

Tyr Arg Asn Leu Leu Trp Leu Thr Val Lys Asn Gly Leu Tyr Pro Asn
                165                 170                 175

Leu Ser Lys Ser Tyr Thr Asn Lys Lys Glu Lys Glu Val Leu Val Leu
            180                 185                 190

Trp Gly Val His His Pro Ser Asn Ile Gly Asp Gln Arg Ala Leu Tyr
            195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asn Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Glu
            260                 265                 270

Leu Ser Lys Gly Phe Gly Ser Gly Ile Ile Thr Ser Asn Ala Pro Met
            275                 280                 285

Gly Glu Cys Asn Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Lys Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Gln Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
```

-continued

```
            465                 470                 475                 480
    Phe Glu Phe Tyr His Lys Cys Asn Asp Glu Cys Met Glu Ser Val Lys
                    485                 490                 495

Asn Gly Thr Tyr Asp Tyr Pro Lys Tyr Ser Glu Glu Ser Lys Leu Asn
                    500                 505                 510

Arg Glu Lys Ile Asp Gly Val Lys Leu Glu Ser Met Gly Val Tyr Asn
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
    545                 550                 555                 560

Cys Arg Ile Cys Ile
                    565
```